US012668839B2

(12) United States Patent　　　(10) Patent No.: US 12,668,839 B2
Fisher et al.　　　　　　　　　　　(45) Date of Patent: Jun. 30, 2026

(54) METHODS FOR IMPROVING POLYNUCLEOTIDE CLUSTER CLONALITY

(71) Applicant: Illumina, Inc., San Diego, CA (US)

(72) Inventors: Jeffrey S. Fisher, San Diego, CA (US); Minghao Guo, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 470 days.

(21) Appl. No.: 16/719,516

(22) Filed: Dec. 18, 2019

(65) Prior Publication Data

US 2020/0208214 A1　　　Jul. 2, 2020

Related U.S. Application Data

(60) Provisional application No. 62/782,279, filed on Dec. 19, 2018.

(51) Int. Cl.
　　*C12Q 1/68*　　　　(2018.01)
　　*C12Q 1/6806*　　　(2018.01)
　　*C12Q 1/6844*　　　(2018.01)
　　*C12Q 1/6874*　　　(2018.01)

(52) U.S. Cl.
　　CPC ......... *C12Q 1/6874* (2013.01); *C12Q 1/6806* (2013.01); *C12Q 1/6844* (2013.01)

(58) Field of Classification Search
　　None
　　See application file for complete search history.

(56) References Cited

U.S. PATENT DOCUMENTS

2002/0177141 A1* 11/2002 Chee ..................... C12Q 1/6874
　　　　　　　　　　　　　　　　　　　506/4
2004/0067559 A1　 4/2004 McCarthy et al.
2007/0128624 A1* 6/2007 Gormley .............. C12Q 1/6855
　　　　　　　　　　　　　　　　　　　435/6.12

2009/0233802 A1* 9/2009 Bignell ................ C12Q 1/6874
　　　　　　　　　　　　　　　　　　　506/2
2009/0311754 A1* 12/2009 Seitz .................... C12Q 1/6853
　　　　　　　　　　　　　　　　　　　435/91.2
2013/0338042 A1* 12/2013 Shen .................... C12Q 1/6844
　　　　　　　　　　　　　　　　　　　506/26
2016/0362748 A1* 12/2016 Mongan .............. C12Q 1/6827
2018/0037950 A1　 2/2018 Gunderson et al.

FOREIGN PATENT DOCUMENTS

| JP | 2015519084 A | 7/2015 | |
| JP | 2017533710 A | 11/2017 | |
| RU | 2284357 C2 | 9/2006 | |
| WO | WO-2004070005 A2 * | 8/2004 | ........ B01L 3/502707 |
| WO | 2015134552 | 9/2015 | |
| WO | 2016075204 | 5/2016 | |
| WO | WO-2016075204 A1 * | 5/2016 | .......... B01J 19/0046 |

OTHER PUBLICATIONS

International Preliminary Report on Patentability for PCT/US2019/067233, issued by the International Bureau of WIPO, Jul. 1, 2021; 8 pgs.
International Search Report and Written Opinion for PCT/US2019/067233 issued by the European Patent Office, Apr. 1, 2020; 15 pgs.
Harkins et al., "A novel NGS library preparation method to characterize native termini of fragmented DNA," Nucl Acid Research, 2020;48(8): e47: 13 pgs.
Wang et al., "3' Branch Ligation A Novel Method to Ligate Non-Complementary DNA to Recessed or Internal 3'OH Ends in DNA or RNA," BioRxIV, Jun. 29, 2018: pp. 1-21.
Office Action in RU2020142082, issued Apr. 6, 2023, 17 pages.

* cited by examiner

*Primary Examiner* — Suryaprabha Chunduru
(74) *Attorney, Agent, or Firm* — Illumina, Inc.

(57)　　　　　ABSTRACT

The present invention is concerned with compositions and methods for improving the generation of monoclonal clusters in an array by tuning the degree of homology between target nucleic acid adapters and the primers attached to the array to encode a kinetic delay into seeded target nucleic acids.

26 Claims, 6 Drawing Sheets

Ratio of final reads coming from each mutant adapter

METHODS FOR IMPROVING POLYNUCLEOTIDE CLUSTER CLONALITY

PRIORITY

This application claims the benefit of U.S. Provisional Application No. 62/782,279, filed Dec. 19, 2018, the disclosure of which is incorporated by reference herein in its entirety.

FIELD

The present disclosure relates to, among other things, the use of exclusion amplification of target nucleic acids to generate clusters of sequencing of amplicons; and more particularly to increasing the number of clusters that are monoclonal.

BACKGROUND

Improvements in next-generation sequencing (NGS) technology have greatly increased sequencing speed and data output, resulting in the massive sample throughput of current sequencing platforms. Approximately 10 years ago, the Illumina Genome Analyzer was capable of generating up to 1 gigabyte of sequence data per run. Today, the Illumina NovaSeq™ Series of Systems are capable of generating up to 2 terabytes of data in two days, which represents a greater than 2000× increase in capacity.

One aspect of realizing this increased capacity is cluster generation. Cluster generation can include production of a library where the members of the library include a universal sequence present at each end. The library is loaded into a flow cell and individual members of the library are captured on a lawn of surface-bound oligos complementary to the universal sequence. Each member is then amplified into distinct clonal clusters through bridge amplification. When cluster generation is complete an individual cluster can include roughly 1000 copies of a single member of the library, and the library is ready for sequencing.

One method of bridge amplification is exclusion amplification (ExAmp), also known as kinetic exclusion amplification. This method is a recombinase-facilitated amplification reaction that uses a patterned array and isothermal conditions to amplify the library, resulting in faster amplification and use of fewer reagents to generate clonal clusters in wells of an array. ExAmp methods have proven to be very useful for the generation of clonal clusters; however, conditions that result in more occupied wells also cause production of more polyclonal wells.

SUMMARY OF THE APPLICATION

Next generation sequencing (NGS) technology relies on the highly parallel sequencing of monoclonal populations of amplicons that were produced from a single target nucleic acid. Sequencing monoclonal populations of amplicons yields much higher signal-to-noise ratios, increased intensity, and increased percentage of clusters that pass filter, all of which contribute to increased data output and data quality.

Exclusion amplification methods allow for the amplification of a single target nucleic per well on a patterned flow cell and the production of a monoclonal population of amplicons in a well. Typically, the rate of amplification of the first captured target nucleic acid within a well is more rapid relative to much slower rates of transport and capture of the target nucleic acid at the well. The first target nucleic acid captured in a well can be amplified rapidly and fill the entire well, preventing the capture of additional target nucleic acids in the same well. Alternatively, if a second target nucleic acid attaches to same well after the first, the rapid amplification of the first often fills enough of the well to result in a signal that passes filter. The use of exclusion amplification can also result in super-Poisson distributions of monoclonal wells, i.e., the fraction of wells in an array that are monoclonal can exceed the fraction predicted by the Poisson distribution.

Increasing super-Poisson distributions of useful clusters is highly desirable because more monoclonal wells result in more data output; however, the seeding of target nucleic acids into wells generally follows a spatial Poisson distribution, where the trade-off for more occupied wells is more polyclonal wells. One method of obtaining higher super-Poisson distributions is to have seeding occur quickly, followed by a delay among the seeded target nucleic acids. The delay, termed "kinetic delay" because it is thought to arise through the biochemical reaction kinetics, gives one seeded target nucleic acid an earlier start over the other seeded targets.

Exclusion amplification works by using recombinase to facilitate the invasion of primers (e.g., primers attached to a well) into double-stranded DNA (e.g., a target nucleic acid) when it finds a sequence match. In order to maximize the amplification efficiency, it is standard practice for exclusion amplification to use complete identity between the invasion primers and the adapter sequences. The inventors have identified a way to encode a kinetic delay into seeded target nucleic acids by tuning the degree of homology between the target nucleic acid adapters and the primers attached to the wells. By reducing the average homology between invasion primers and adapter sequences, there was a surprising improvement in the rate of called monoclonality of the wells, even though the average rate of amplification was reduced. In general, as more mismatches were introduced, the amplification efficiency decreased. Unexpectedly, when mixtures of adapter sequences having both higher and lower amplification efficiencies were used, the mixtures did not perform as an average of the performance of the individual components—halfway between the high and low efficiencies—but outperformed all single-type adapter sequences in both intensity and clusters passing filter.

Definitions

Terms used herein will be understood to take on their ordinary meaning in the relevant art unless specified otherwise. Several terms used herein and their meanings are set forth below.

As used herein, the term "amplicon," when used in reference to a nucleic acid, means the product of copying the nucleic acid, wherein the product has a nucleotide sequence that is the same as or complementary to at least a portion of the nucleotide sequence of the nucleic acid. An amplicon can be produced by any of a variety of amplification methods that use the nucleic acid, e.g., a target nucleic acid or an amplicon thereof, as a template including, for example, polymerase extension, polymerase chain reaction (PCR), rolling circle amplification (RCA), ligation extension, or ligation chain reaction. An amplicon can be a nucleic acid molecule having a single copy of a particular nucleotide sequence (e.g. a polymerase extension product) or multiple copies of the nucleotide sequence (e.g. a concatemeric product of RCA). A first amplicon of a target nucleic acid is typically a complementary copy. Subsequent amplicons are copies that are created, after generation of the first amplicon, from the target nucleic acid or from the first amplicon. A subsequent amplicon can have a sequence that is substantially complementary to the target nucleic acid or substantially identical to the target nucleic acid.

As used herein, the term "amplification site" refers to a site in or on an array where one or more amplicons can be generated. An amplification site can be further configured to contain, hold or attach at least one amplicon that is generated at the site.

As used herein, the term "array" refers to a population of sites that can be differentiated from each other according to relative location. Different molecules that are at different sites of an array can be differentiated from each other according to the locations of the sites in the array. An individual site of an array can include one or more molecules of a particular type. For example, a site can include a single target nucleic acid molecule having a particular sequence or a site can include several nucleic acid molecules having the same sequence (and/or complementary sequence, thereof). The sites of an array can be different features located on the same substrate. Exemplary features include without limitation, wells in a substrate, beads (or other particles) in or on a substrate, projections from a substrate, ridges on a substrate or channels in a substrate. The sites of an array can be separate substrates each bearing a different molecule. Different molecules attached to separate substrates can be identified according to the locations of the substrates on a surface to which the substrates are associated or according to the locations of the substrates in a liquid or gel. Exemplary arrays in which separate substrates are located on a surface include, without limitation, those having beads in wells.

As used herein, the term "capacity," when used in reference to a site and nucleic acid material, means the maximum amount of nucleic acid material, e.g., amplicons derived from a target nucleic acid, that can occupy the site. For example, the term can refer to the total number of nucleic acid molecules that can occupy the site in a particular condition. Other measures can be used as well including, for example, the total mass of nucleic acid material or the total number of copies of a particular nucleotide sequence that can occupy the site in a particular condition. Typically, the capacity of a site for a target nucleic acid will be substantially equivalent to the capacity of the site for amplicons of the target nucleic acid.

As used herein, the term "capture agent" refers to a material, chemical, molecule, or moiety thereof that is capable of attaching, retaining, or binding to a target molecule (e.g. a target nucleic acid). Exemplary capture agents include, without limitation, a capture nucleic acid that is complementary to at least a portion of a modified target nucleic acid (e.g., a universal capture binding sequence), a member of a receptor-ligand binding pair (e.g. avidin, streptavidin, biotin, lectin, carbohydrate, nucleic acid binding protein, epitope, antibody, etc.) capable of binding to a modified target nucleic acid (or linking moiety attached thereto), or a chemical reagent capable of forming a covalent bond with a modified target nucleic acid (or linking moiety attached thereto). In one embodiment, a capture agent is a nucleic acid. A nucleic acid capture agent can also be used as an amplification primer.

The terms "P5" and "P7" may be used when referring to a nucleic acid capture agent. The terms "P5'" (P5 prime) and "P7'" (P7 prime) refer to the complements of P5 and P7, respectively. It will be understood that any suitable nucleic acid capture agent can be used in the methods presented herein, and that the use of P5 and P7 are exemplary embodiments only. Uses of nucleic acid capture agents such as P5 and P7 on flowcells is known in the art, as exemplified by the disclosures of WO 2007/010251, WO 2006/064199, WO 2005/065814, WO 2015/106941, WO 1998/044151, and WO 2000/018957. One of skill in the art will recognize that a nucleic acid capture agent can also function as an amplification primer. For example, any suitable nucleic acid capture agent can act as a forward amplification primer, whether immobilized or in solution, and can be useful in the methods presented herein for hybridization to a sequence (e.g., a universal capture binding sequence) and amplification of a sequence. Similarly, any suitable nucleic acid capture agent can act as a reverse amplification primer, whether immobilized or in solution, and can be useful in the methods presented herein for hybridization to a sequence (e.g., a universal capture binding sequence) and amplification of a sequence. In view of the general knowledge available and the teachings of the present disclosure, one of skill in the art will understand how to design and use sequences that are suitable for capture and amplification of target nucleic acids as presented herein.

As used herein, the term "universal sequence" refers to a region of sequence that is common to two or more target nucleic acids, where the molecules also have regions of sequence that differ from each other. A universal sequence that is present in different members of a collection of molecules can allow capture of multiple different nucleic acids using a population of capture nucleic acids that are complementary to a portion of the universal sequence, e.g., a universal capture binding sequence. Non-limiting examples of universal capture binding sequences include sequences that are identical to or complementary to P5 and P7 primers. Other non-limiting examples of universal capture binding sequences described in detail herein include sequences with reduced identity (e.g., one or more mismatches) or reduced complementarity to P5 and P7 primers, and/or have a length that is less than a P5 and P7 primers. Similarly, a universal sequence present in different members of a collection of molecules can allow the replication or amplification of multiple different nucleic acids using a population of universal primers that are complementary to a portion of the universal sequence, e.g., a universal primer binding site. Target nucleic acid molecules may be modified to attach universal adapters (also referred to herein as adapters), for example, at one or both ends of the different target sequences, as described herein.

As used herein, the term "adapter" and its derivatives, e.g., universal adapter, refers generally to any linear oligonucleotide which can be ligated to a target nucleic acid. In some embodiments, the adapter is substantially non-complementary to the 3' end or the 5' end of any target sequence present in a sample. In some embodiments, suitable adapter lengths are in the range of about 10-100 nucleotides, about 12-60 nucleotides and about 15-50 nucleotides in length. Generally, the adapter can include any combination of nucleotides and/or nucleic acids. In some aspects, the adapter can include one or more cleavable groups at one or more locations. In another aspect, the adapter can include a sequence that is substantially identical, or substantially complementary, to at least a portion of a primer, for example a capture nucleic acid. In some embodiments, the adapter can include a barcode, also referred to as an index or tag, to assist with downstream error correction, identification, or sequencing. The terms "adaptor" and "adapter" are used interchangeably.

As defined herein, "sample" and its derivatives is used in its broadest sense and includes any specimen, culture and the like that is suspected of including a target nucleic acid. In some embodiments, the sample comprises DNA, RNA, PNA, LNA, chimeric or hybrid forms of nucleic acids. The sample can include any biological, clinical, surgical, agricultural, atmospheric or aquatic-based specimen containing one or more nucleic acids. The term also includes any isolated nucleic acid sample such a genomic DNA, fresh-frozen or formalin-fixed paraffin-embedded nucleic acid specimen. It is also envisioned that the sample can be from a single individual, a collection of nucleic acid samples from genetically related members, nucleic acid samples from genetically unrelated members, nucleic acid samples (matched) from a single individual such as a tumor sample and normal tissue sample, or sample from a single source that contains two distinct forms of genetic material such as maternal and fetal DNA obtained from a maternal subject, or the presence of contaminating bacterial DNA in a sample that contains plant or animal DNA. In some embodiments, the source of nucleic acid material can include nucleic acids obtained from a newborn, for example as typically used for newborn screening.

As used herein, the term "clonal population" refers to a population of nucleic acids that is homogeneous with respect to a particular nucleotide sequence. The homogenous sequence is typically at least 10 nucleotides long, but can be even longer including for example, at least 50, at least 100, at least 250, at least 500, or at least 1000 nucleotides long. A clonal population can be derived from a single target nucleic acid. Typically, all of the nucleic acids in a clonal population will have the same nucleotide sequence. It will be understood that a small number of mutations (e.g. due to amplification artifacts) can occur in a clonal population without departing from clonality. It will also be understood that a small number of different target nucleic acid (e.g., due to a target nucleic acid that was not amplified or amplified to a limited degree) can occur in a clonal population without departing from clonality.

As used herein, the term "different," when used in reference to nucleic acids, means that the nucleic acids have nucleotide sequences that are not the same as each other. Two or more nucleic acids can have nucleotide sequences that are different along their entire length. Alternatively, two or more nucleic acids can have nucleotide sequences that are different along a substantial portion of their length. For example, two or more nucleic acids can have target nucleotide sequence portions that are different from each other while also having a universal sequence region that are the same as each other.

As used herein, the term "fluidic access," when used in reference to a molecule in a fluid and a site in contact with the fluid, refers to the ability of the molecule to move in or through the fluid to contact or enter the site. The term can also refer to the ability of the molecule to separate from or exit the site to enter the solution. Fluidic access can occur when there are no barriers that prevent the molecule from entering the site, contacting the site, separating from the site and/or exiting the site. However, fluidic access is understood to exist even if diffusion is retarded, reduced or altered so long as access is not absolutely prevented.

As used herein, the term "double stranded," when used in reference to a nucleic acid molecule, means that substantially all of the nucleotides in the nucleic acid molecule are hydrogen bonded to a complementary nucleotide. A partially double stranded nucleic acid can have at least 10%, at least 25%, at least 50%, at least 60%, at least 70%, at least 80%, at least 90% or at least 95% of its nucleotides hydrogen bonded to a complementary nucleotide.

As used herein, the term "each," when used in reference to a collection of items, is intended to identify an individual item in the collection but does not necessarily refer to every item in the collection unless the context clearly dictates other.

As used herein, the term "excluded volume" refers to the volume of space occupied by a particular molecule to the exclusion of other such molecules.

As used herein, the term "interstitial region" refers to an area in a substrate or on a surface that separates other areas of the substrate or surface. For example, an interstitial region can separate one feature of an array from another feature of the array. The two regions that are separated from each other can be discrete, lacking contact with each other. In another example, an interstitial region can separate a first portion of a feature from a second portion of a feature. The separation provided by an interstitial region can be partial or full separation. Interstitial regions will typically have a surface material that differs from the surface material of the features on the surface. For example, features of an array can have an amount or concentration of capture agents that exceeds the amount or concentration present at the interstitial regions. In some embodiments the capture agents may not be present at the interstitial regions.

As used herein, the term "polymerase" is intended to be consistent with its use in the art and includes, for example, an enzyme that produces a complementary replicate of a nucleic acid molecule using the nucleic acid as a template strand. Typically, DNA polymerases bind to the template strand and then move down the template strand sequentially adding nucleotides to the free hydroxyl group at the 3' end of a growing strand of nucleic acid. DNA polymerases typically synthesize complementary DNA molecules from DNA templates and RNA polymerases typically synthesize RNA molecules from DNA templates (transcription). Polymerases can use a short RNA or DNA strand, called a primer, to begin strand growth. Some polymerases can displace the strand upstream of the site where they are adding bases to a chain. Such polymerases are said to be strand displacing, meaning they have an activity that removes a complementary strand from a template strand being read by the polymerase. Exemplary polymerases having strand displacing activity include, without limitation, the large fragment of Bsu (*Bacillus subtilis*), Bst (*Bacillus stearothermophilus*) polymerase, exo-Klenow polymerase or sequencing grade T7 exo-polymerase. Some polymerases degrade the strand in front of them, effectively replacing it with the growing chain behind (5' exonuclease activity). Some polymerases have an activity that degrades the strand behind them (3' exonuclease activity). Some useful polymerases have been modified, either by mutation or otherwise, to reduce or eliminate 3' and/or 5' exonuclease activity.

As used herein, the term "nucleic acid" is intended to be consistent with its use in the art and includes naturally occurring nucleic acids and functional analogs thereof. Particularly useful functional analogs are capable of hybridizing to a nucleic acid in a sequence specific fashion or capable of being used as a template for replication of a particular nucleotide sequence. Naturally occurring nucleic acids generally have a backbone containing phosphodiester bonds. An analog structure can have an alternate backbone linkage including any of a variety of those known in the art. Naturally occurring nucleic acids generally have a deoxyribose sugar (e.g. found in deoxyribonucleic acid (DNA)) or a ribose sugar (e.g. found in ribonucleic acid (RNA)). A nucleic acid can contain any of a variety of analogs of these sugar moieties that are known in the art. A nucleic acid can include native or non-native bases. In this regard, a native deoxyribonucleic acid can have one or more bases selected from adenine, thymine, cytosine or guanine and a ribonucleic acid can have one or more bases selected from uracil, adenine, cytosine or guanine. Useful non-native bases that can be included in a nucleic acid are known in the art. The term "target," when used in reference to a nucleic acid, is intended as a semantic identifier for the nucleic acid in the context of a method or composition set forth herein and does not necessarily limit the structure or function of the nucleic acid beyond what is otherwise explicitly indicated. A target nucleic acid having a universal sequence at each end, for instance a universal adapter at each end, can be referred to as a modified target nucleic acid.

As used herein, the terms "recombinase loading protein" and "recombinase" are used interchangeably and are intended to be consistent with its use in the art and include, for example, RecA protein, the T4 UvsX protein, the RB69 bacteriophage UvsX protein, any homologous protein or protein complex from any phyla, or functional variants thereof. Eukaryotic RecA homologues are generally named Rad51 after the first member of this group to be identified. Other non-homologous recombinases may be used in place of RecA, for example, RecT or RecO.

As used herein, the term "single stranded binding protein," also referred to as "SSB protein" or "SSB," is intended to refer to any protein having a function of binding to a single stranded nucleic acid, for example, to prevent premature annealing, to protect the single-stranded nucleic acid from nuclease digestion, to remove secondary structure from the nucleic acid, or to facilitate replication of the nucleic acid. The term is intended to include, but is not limited to, proteins that are formally identified as Single Stranded Binding proteins by the Nomenclature Committee of the International Union of Biochemistry and Molecular Biology (NC-IUBMB). Exemplary single stranded binding proteins include, but are not limited to E. coli SSB, T4 gp32, T7 gene 2.5 SSB, phage phi 29 SSB, RB69 bacteriophage gp32 protein, any homologous protein or protein complex from any phyla, and functional variants thereof.

As used herein, the term "accessory protein" is intended to refer to any protein having a function of interacting with a recombinase and single stranded binding protein to aid in production of nucleation of a UvsX filament on a ssDNA. The terms "accessory protein," "recombinase accessory protein," and "recombinase helper protein" are used interchangeably. Exemplary accessory proteins include, but are not limited to T4 UvsY, RB69 bacteriophage UvsY protein, E. coli RecO, E. coli RecR, any homologous protein or protein complex from any phyla, and functional variants thereof.

As used herein, the term "transport" refers to movement of a molecule through a fluid. The term can include passive transport such as movement of molecules along their concentration gradient (e.g. passive diffusion). The term can also include active transport whereby molecules can move along their concentration gradient or against their concentration gradient. Thus, transport can include applying energy to move one or more molecule in a desired direction or to a desired location such as an amplification site.

As used herein, the term "rate," when used in reference to transport, amplification, capture or other chemical processes, is intended to be consistent with its meaning in chemical kinetics and biochemical kinetics. Rates for two processes can be compared with respect to maximum rates (e.g. at saturation), pre-steady state rates (e.g. prior to equilibrium), kinetic rate constants, or other measures known in the art. In particular embodiments, a rate for a particular process can be determined with respect to the total time for completion of the process. For example, an amplification rate can be determined with respect to the time taken for amplification to be complete. However, a rate for a particular process need not be determined with respect to the total time for completion of the process.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

It is understood that wherever embodiments are described herein with the language "include," "includes," or "including," and the like, otherwise analogous embodiments described in terms of "consisting of and/or" consisting essentially of are also provided.

Unless otherwise specified, "a," "an," "the," and "at least one" are used interchangeably and mean one or more than one.

Conditions that are "suitable" for an event to occur, such as hybridization of two nucleic acid sequences, or "suitable" conditions are conditions that do not prevent such events from occurring. Thus, these conditions permit, enhance, facilitate, and/or are conducive to the event.

As used herein, "providing" in the context of a composition, an article, or a nucleic acid means making the composition, article, or nucleic acid, purchasing the composition, article, or nucleic acid, or otherwise obtaining the compound, composition, article, or nucleic acid.

Also herein, the recitations of numerical ranges by endpoints include all numbers subsumed within that range (e.g., 1 to 5 includes 1, 1.5, 2, 2.75, 3, 3.80, 4, 5, etc.).

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

The following detailed description of illustrative embodiments of the present disclosure may be best understood when read in conjunction with the following drawings.

In FIG. 4A, a recombinase facilitates the invasion of free P7 primers into double-stranded templates containing homologous sequences (i.e. matching P7 ends). Perfect homology is not required (here shown by two deliberate mismatches introduced to P7), but the rate of invasion and amplification will be decreased by the reduced homology adapters (here depicted by a smaller arrow for mutant strands). In FIG. 4B, recombinase-mediated invasion from either end occurs with an unmutated lawn-primer and effectively corrects the mutations from the daughter strands, thereby transforming them back into perfect adapters. However, since the homology between the original strand and the lawn strand has been reduced, the time-delay until the first copy occurs is proportional to the number and degree of mutations.

In FIG. 5A, one successful copy transforms each template into a perfect one. However, the time constant for that transition depends on the degree of non-homology to overcome (greater rates are indicated by thicker arrows). In FIG. 5B, the slower rates of amplification in short and mutant adapter libraries are indicated by the rightward shifts in the real-time amplification curves.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar to other numbered components.

DETAILED DESCRIPTION

Provided herein are compositions and methods related to increasing the production of monoclonal clusters that can be used in sequencing.

Figure 1A:
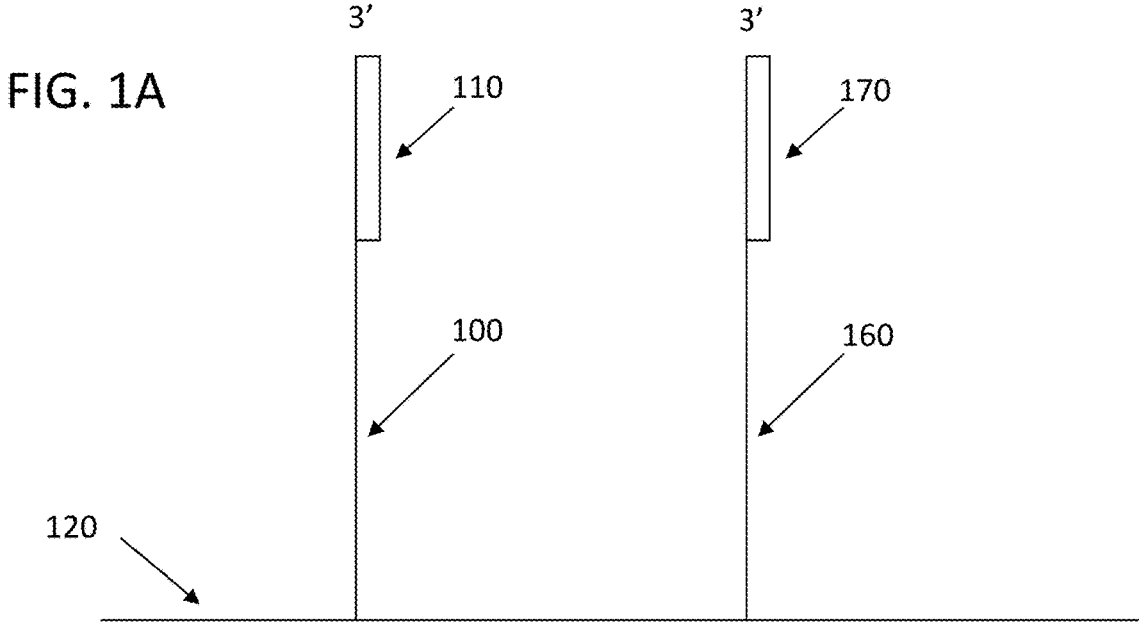
FIGS. 1A and 1B are a schematic of an illustrative example or a first and a second capture sequence attached to a well of an array (FIG. 1A), and a schematic of an illustrative example of a target nucleic acid having a universal adapter attached to each end (FIG. 1B).
Figure 1B:
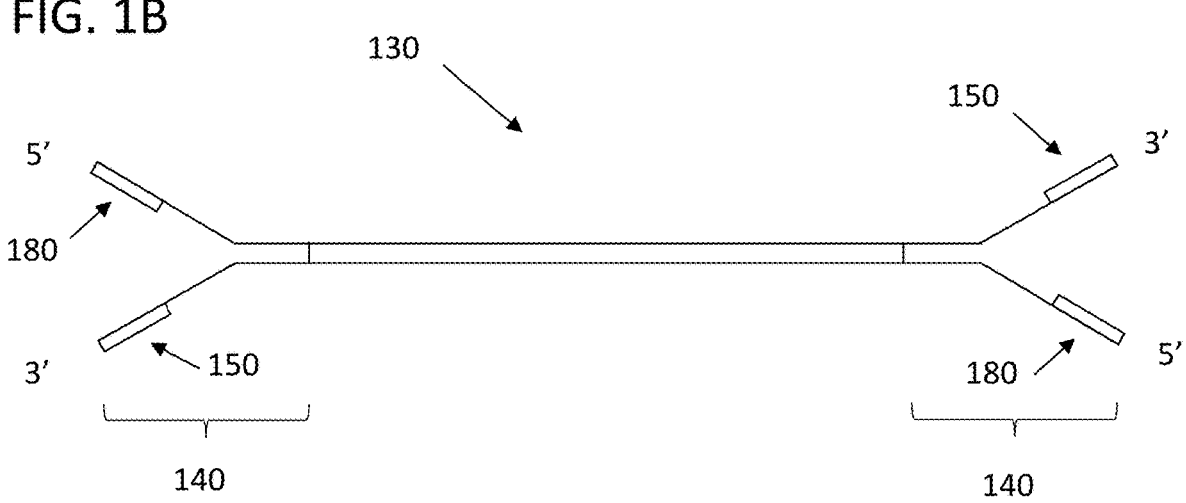

The present disclosure provides methods for amplifying nucleic acids and methods for determining nucleic acid sequences. In one embodiment, a method includes providing an amplification reagent that includes (i) an array of amplification sites, and (ii) a solution having a plurality of different target nucleic acids. The amplification sites include at least two populations of capture nucleic acids. One population, a first population, includes a first capture sequence and the second population includes a second capture sequence. The different target nucleic acids include at the 3' end a first universal capture binding sequence. In one embodiment the target nucleic acids are double-stranded. The first universal capture binding sequence has less affinity for the first capture sequence than a first universal capture binding sequence having 100% complementarity with the first capture sequence. For instance, as shown in FIG. 1A, a nucleic acid 100 of a first population of capture nucleic acids includes a first capture sequence 110, where the nucleic acid 100 is attached to the surface of an amplification site 120. Shown in FIG. 1B is a double stranded target nucleic acid 130 that includes a universal adapter 140 at each end, and a first universal capture binding sequence 150 at the 3' end of each universal adapter 140.

Optionally, the different target nucleic acids also include at the 5' end a second universal capture binding sequence. The complement of the second universal capture binding sequence has less affinity for the second capture sequence than a second universal capture binding sequence having a complement with 100% complementarity to the second capture sequence. For instance, as shown in FIG. 1A, a nucleic acid 160 of a second population of capture nucleic acids includes a first capture sequence 170, where the nucleic acid 160 is attached to the surface of an amplification site 120. Shown in FIG. 1B is a double stranded target nucleic acid 130 that includes a universal adapter 140 at each end, and a second universal capture binding sequence 180 at the 5' end of each universal adapter 140.

Figure 2:
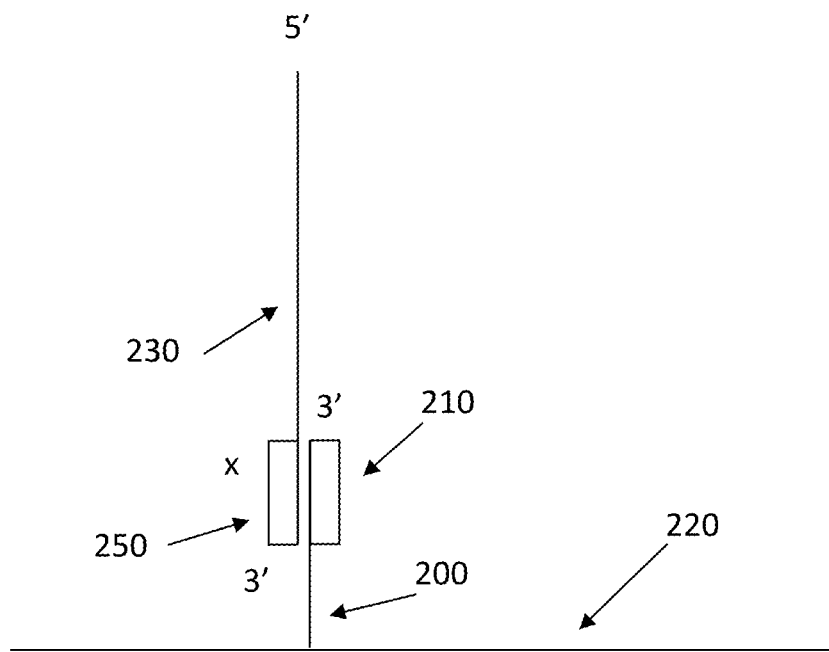
FIG. 2 is a schematic of an illustrative example of a first capture nucleic acid attached to a well of an array and a hybridized single strand of a target nucleic acid.

The method further includes reacting the amplification reagent to produce a plurality of amplification sites that each have a clonal population of amplicons from an individual target nucleic acid from the solution. The reacting includes transporting the different target nucleic acids to the amplification sites and amplifying the target nucleic acids at the amplification sites. For instance, as shown in FIG. 2, a nucleic acid 200 of a first population of capture nucleic acids includes a first capture sequence 210, where the nucleic acid 200 is attached to the surface of an amplification site 220. One strand of a target nucleic acid 230 that includes a first universal capture binding sequence 250 at the 3' end of single strand is hybridized to the first capture sequence 210 of the nucleic acid 200. The first universal capture binding sequence 250 includes an 'X' to signify the presence of a mismatch between the first universal capture binding sequence 250 and the first capture sequence 210. This can then undergo cluster amplification, for instance via bridge amplification, to result in the generation of a cluster.

Also provided herein is a method for producing a library of nucleic acids. The library can be used in the method for amplifying described herein. The method includes providing a solution of a plurality of different target nucleic acids. In one embodiment the target nucleic acids are double-stranded. A universal adapter is ligated to both ends of the double-stranded target nucleic acids to form a first plurality of modified target nucleic acids, where each of the modified target nucleic acids includes a target nucleic acid flanked by the universal adapter. The universal adapter includes a region of double stranded nucleic acid and a region of single-stranded non-complementary nucleic acid strands. The region of single-stranded non-complementary nucleic acid strands include at the 3' ends a first universal capture binding sequence. The first universal capture binding sequence has less affinity for a first capture sequence than a first universal capture binding sequence having 100% complementarity with the first capture sequence. Optionally, the region of single-stranded non-complementary nucleic acid strands include at the 5' end a second universal capture binding sequence. The complement of the second universal capture binding sequence has less affinity for a second capture sequence than a second universal capture binding sequence having a complement with 100% complementarity to the second capture sequence.

Arrays

An array of amplification sites used in a method set forth herein can be present as one or more substrates. Exemplary types of substrate materials that can be used for an array include glass, modified glass, functionalized glass, inorganic glasses, microspheres (e.g. inert and/or magnetic particles), plastics, polysaccharides, nylon, nitrocellulose, ceramics, resins, silica, silica-based materials, carbon, metals, an optical fiber or optical fiber bundles, polymers and multiwell (e.g. microtiter) plates. Exemplary plastics include acrylics, polystyrene, copolymers of styrene and other materials, polypropylene, polyethylene, polybutylene, polyurethanes and Teflon™. Exemplary silica-based materials include silicon and various forms of modified silicon.

In particular embodiments, a substrate can be within or part of a vessel such as a well, tube, channel, cuvette, Petri plate, bottle or the like. A particularly useful vessel is a flow-cell, for example, as described in U.S. Pat. No. 8,241,573 or Bentley et al., Nature 456:53-59 (2008). Exemplary flow-cells are those that are commercially available from Illumina, Inc. (San Diego, Calif.). Another particularly useful vessel is a well in a multiwell plate or microtiter plate.

In some embodiments, the sites of an array can be configured as features on a surface. The features can be present in any of a variety of desired formats. For example, the sites can be wells, pits, channels, ridges, raised regions, pegs, posts or the like. As set forth above, the sites can contain beads. However, in particular embodiments the sites need not contain a bead or particle. Exemplary sites include wells that are present in substrates used for commercial sequencing platforms sold by 454 LifeSciences (a subsidiary of Roche, Basel Switzerland) or Ion Torrent (a subsidiary of Life Technologies, Carlsbad Calif.). Other substrates having wells include, for example, etched fiber optics and other substrates described in U.S. Pat. Nos. 6,266,459; 6,355,431; 6,770,441; 6,859,570; 6,210,891; 6,258,568; 6,274,320; 8,262,900; 7,948,015; U.S. Pat. Pub. No. 2010/0137143; U.S. Pat. No. 8,349,167, or PCT Publication No. WO 00/63437. In several cases the substrates are exemplified in these references for applications that use beads in the wells. The well-containing substrates can be used with or without beads in the methods or compositions of the present disclosure. In some embodiments, wells of a substrate can include gel material (with or without beads) as set forth in U.S. Pat. No. 9,512,422.

The sites of an array can be metal features on a nonmetallic surface such as glass, plastic or other materials exemplified above. A metal layer can be deposited on a surface using methods known in the art such as wet plasma etching, dry plasma etching, atomic layer deposition, ion beam etching, chemical vapor deposition, vacuum sputtering or the like. Any of a variety of commercial instruments can be used as appropriate including, for example, the FlexAL®, OpAL®, Ionfab 300Plus®, or Optofab 3000® systems (Oxford Instruments, UK). A metal layer can also be deposited by e-beam evaporation or sputtering as set forth in Thornton, Ann. Rev. Mater. Sci. 7:239-60 (1977). Metal layer deposition techniques, such as those exemplified above, can be combined with photolithography techniques to create metal regions or patches on a surface. Exemplary methods for combining metal layer deposition techniques and photolithography techniques are provided in U.S. Pat. Nos. 8,778,848 and 8,895,249.

An array of features can appear as a grid of spots or patches. The features can be located in a repeating pattern or in an irregular non-repeating pattern. Particularly useful patterns are hexagonal patterns, rectilinear patterns, grid patterns, patterns having reflective symmetry, patterns having rotational symmetry, or the like. Asymmetric patterns can also be useful. The pitch can be the same between different pairs of nearest neighbor features or the pitch can vary between different pairs of nearest neighbor features. In particular embodiments, features of an array can each have an area that is larger than about 100 nm2, 250 nm2, 500 nm2, 1 μm2, 2.5 μm2, 5 μm2, 10 μm2, 100 μm2, or 500 μm2. Alternatively, or additionally, features of an array can each have an area that is smaller than about 1 mm2, 500 μm2, 100 μm2, 25 μm2, 10 μm2, 5 μm2, 1 μm2, 500 nm2, or 100 nm2. Indeed, a region can have a size that is in a range between an upper and lower limit selected from those exemplified above.

For embodiments that include an array of features on a surface, the features can be discrete, being separated by interstitial regions. The size of the features and/or spacing between the regions can vary such that arrays can be high density, medium density or lower density. High density arrays are characterized as having regions separated by less than about 15 μm. Medium density arrays have regions separated by about 15 to 30 μm, while low density arrays have regions separated by greater than 30 μm. An array useful in the disclosure can have regions that are separated by less than 100 μm, 50 μm, 10 μm, 5 μm, 1 μm or 0.5 μm.

In particular embodiments, an array can include a collection of beads or other particles. The particles can be suspended in a solution or they can be located on the surface of a substrate. Examples of bead arrays in solution are those commercialized by Luminex (Austin, Tex.). Examples of arrays having beads located on a surface include those wherein beads are located in wells such as a BeadChip array (Illumina Inc., San Diego Calif.) or substrates used in sequencing platforms from 454 LifeSciences (a subsidiary of Roche, Basel Switzerland) or Ion Torrent (a subsidiary of Life Technologies, Carlsbad Calif.). Other arrays having beads located on a surface are described in U.S. Pat. Nos. 6,266,459; 6,355,431; 6,770,441; 6,859,570; 6,210,891; 6,258,568; 6,274,320; US 2009/0026082 A1; US 2009/0127589 A1; US 2010/0137143 A1; US 2010/0282617 A1 or PCT Publication No. WO 00/63437. Several of the above references describe methods for attaching target nucleic acids to beads prior to loading the beads in or on an array substrate. It will however, be understood that the beads can be made to include amplification primers and the beads can then be used to load an array, thereby forming amplification sites for use in a method set forth herein. As set forth previously herein, the substrates can be used without beads. For example, amplification primers can be attached directly to the wells or to gel material in wells. Thus, the references are illustrative of materials, compositions or apparatus that can be modified for use in the methods and compositions set forth herein.

Amplification sites of an array can include a plurality of capture agents capable of binding to target nucleic acids. In one embodiment, a capture agent includes a capture nucleic acid. In typical conditions used to prepare arrays for sequencing, the nucleotide sequence of the capture nucleic acid is complementary to a sequence of one or more target nucleic acids. In contrast, the nucleotide sequence of the capture nucleic acid of the present disclosure is not completely complementary to a sequence of one or more target nucleic acids. The nucleotide sequence of capture nucleic acids useful in the methods presented in the present disclosure are described in detail herein. In some embodiments, the capture nucleic acid can also function as a primer for amplification of the target nucleic acid (whether or not it also contains a universal sequence). In some embodiments, one population of capture nucleic acid includes a P5 primer or the complement thereof, and the second population of capture nucleic acid includes a P7 primer or the complement thereof.

In particular embodiments, a capture agent, such as a capture nucleic acid, can be attached to the amplification site. For example, the capture agent can be attached to the surface of a feature of an array. The attachment can be via an intermediate structure such as a bead, particle or gel. An example of attachment of capture nucleic acids to an array via a gel is described in U.S. Pat. No. 8,895,249 and further exemplified by flow cells available commercially from Illumina Inc. (San Diego, Calif.) or described in WO 2008/093098. Exemplary gels that can be used in the methods and apparatus set forth herein include, but are not limited to, those having a colloidal structure, such as agarose; polymer mesh structure, such as gelatin; or cross-linked polymer structure, such as polyacrylamide, SFA (see, for example, US Pat. App. Pub. No. 2011/0059865 A1) or PAZAM (see, for example, U.S. Prov. Pat. App. Ser. No. 61/753,833 and U.S. Pat. No. 9,012,022). Attachment via a bead can be achieved as exemplified in the description and cited references set forth previously herein.

In some embodiments, the features on the surface of an array substrate are non-contiguous, being separated by interstitial regions of the surface. Interstitial regions that have a substantially lower quantity or concentration of capture agents, compared to the features of the array, are advantageous. Interstitial regions that lack capture agents are particularly advantageous. For example, a relatively small amount or absence of capture moieties at the interstitial regions favors localization of target nucleic acids, and subsequently generated clusters, to desired features. In particular embodiments, the features can be concave features in a surface (e.g. wells) and the features can contain a gel material. The gel-containing features can be separated from each other by interstitial regions on the surface where the gel is substantially absent or, if present the gel is substantially incapable of supporting localization of nucleic acids. Methods and compositions for making and using substrates having gel containing features, such as wells, are set forth in U.S. Pat. No. 9,512,422.

Target Nucleic Acids

The solution of the amplification reagent used in a method described herein includes target nucleic acids. The terms "target nucleic acid," "target fragment," "target nucleic acid fragment, "target molecule," and "target nucleic acid molecule" are used interchangeably to refer to nucleic acid molecules that it is desired to sequence, such as on an array. The target nucleic acid may be essentially any nucleic acid of known or unknown sequence. It may be, for example, a fragment of genomic DNA or cDNA. Sequencing may result in determination of the sequence of the whole, or a part of the target molecule. The targets can be derived from a primary nucleic acid sample that has been randomly fragmented. In one embodiment, the targets can be processed into templates suitable for amplification by the placement of universal amplification sequences, e.g., sequences present in a universal adaptor, at the ends of each target fragment.

The primary nucleic acid sample may originate in double-stranded DNA (dsDNA) form (e.g. genomic DNA fragments, PCR and amplification products and the like) from a sample or may have originated in single-stranded form from a sample, as DNA or RNA, and been converted to dsDNA form. By way of example, mRNA molecules may be copied into double-stranded cDNAs suitable for use in the method described herein using standard techniques well known in the art. The precise sequence of the polynucleotide molecules from a primary nucleic acid sample is generally not material to the disclosure, and may be known or unknown.

In one embodiment, the primary polynucleotide molecules from a primary nucleic acid sample are DNA molecules. More particularly, the primary polynucleotide molecules represent the entire genetic complement of an organism, and are genomic DNA molecules which include both intron and exon sequences, as well as non-coding regulatory sequences such as promoter and enhancer sequences. In one embodiment, particular sub-sets of polynucleotide sequences or genomic DNA can be used, such as, for example, particular chromosomes. Yet more particularly, the sequence of the primary polynucleotide molecules is not known. Still yet more particularly, the primary polynucleotide molecules are human genomic DNA molecules. The DNA target fragments may be treated chemically or enzymatically either prior or subsequent to any random fragmentation processes, and prior or subsequent to the ligation of the universal adapter sequences.

The nucleic acid sample can include high molecular weight material such as genomic DNA (gDNA). The sample can include low molecular weight material such as nucleic acid molecules obtained from FFPE or archived DNA samples. In another embodiment, low molecular weight material includes enzymatically or mechanically fragmented DNA. The sample can include cell-free circulating DNA. In some embodiments, the sample can include nucleic acid molecules obtained from biopsies, tumors, scrapings, swabs, blood, mucus, urine, plasma, semen, hair, laser capture micro-dissections, surgical resections, and other clinical or laboratory obtained samples. In some embodiments, the sample can be an epidemiological, agricultural, forensic or pathogenic sample. In some embodiments, the sample can include nucleic acid molecules obtained from an animal such as a human or mammalian source. In another embodiment, the sample can include nucleic acid molecules obtained from a non-mammalian source such as a plant, bacteria, virus or fungus. In some embodiments, the source of the nucleic acid molecules may be an archived or extinct sample or species.

Further, the methods and compositions disclosed herein may be useful to amplify a nucleic acid sample having low-quality nucleic acid molecules, such as degraded and/or fragmented genomic DNA from a forensic sample. In one embodiment, forensic samples can include nucleic acids obtained from a crime scene, nucleic acids obtained from a missing persons DNA database, nucleic acids obtained from a laboratory associated with a forensic investigation or include forensic samples obtained by law enforcement agencies, one or more military services or any such personnel. The nucleic acid sample may be a purified sample or a crude DNA containing lysate, for example derived from a buccal swab, paper, fabric or other substrate that may be impregnated with saliva, blood, or other bodily fluids. As such, in some embodiments, the nucleic acid sample may comprise low amounts of, or fragmented portions of DNA, such as genomic DNA. In some embodiments, target sequences can be present in one or more bodily fluids including but not limited to, blood, sputum, plasma, semen, urine and serum. In some embodiments, target sequences can be obtained from hair, skin, tissue samples, autopsy or remains of a victim. In some embodiments, nucleic acids including one or more target sequences can be obtained from a deceased animal or human. In some embodiments, target sequences can include nucleic acids obtained from non-human DNA such a microbial, plant or entomological DNA. In some embodiments, target sequences or amplified target sequences are directed to purposes of human identification. In some embodiments, the disclosure relates generally to methods for identifying characteristics of a forensic sample. In some embodiments, the disclosure relates generally to human identification methods using one or more target specific primers disclosed herein or one or more target specific primers designed using the primer design criteria outlined herein. In one embodiment, a forensic or human identification sample containing at least one target sequence can be amplified using any one or more of the target-specific primers disclosed herein or using the primer criteria outlined herein.

Additional non-limiting examples of sources of biological samples can include whole organisms as well as a sample obtained from a patient. The biological sample can be obtained from any biological fluid or tissue and can be in a variety of forms, including liquid fluid and tissue, solid tissue, and preserved forms such as dried, frozen, and fixed forms. The sample may be of any biological tissue, cells or fluid. Such samples include, but are not limited to, sputum, blood, serum, plasma, blood cells (e.g., white cells), ascitic fluid, urine, saliva, tears, sputum, vaginal fluid (discharge), washings obtained during a medical procedure (e.g., pelvic or other washings obtained during biopsy, endoscopy or surgery), tissue, nipple aspirate, core or fine needle biopsy samples, cell-containing body fluids, free floating nucleic acids, peritoneal fluid, and pleural fluid, or cells therefrom. Biological samples may also include sections of tissues such as frozen or fixed sections taken for histological purposes or micro-dissected cells or extracellular parts thereof. In some embodiments, the sample can be a blood sample, such as, for example, a whole blood sample. In another example, the sample is an unprocessed dried blood spot (DBS) sample. In yet another example, the sample is a formalin-fixed paraffin-embedded (FFPE) sample. In yet another example, the sample is a saliva sample. In yet another example, the sample is a dried saliva spot (DSS) sample.

Exemplary biological samples from which target nucleic acids can be derived include, for example, those from a eukaryote, for instance a mammal, such as a rodent, mouse, rat, rabbit, guinea pig, ungulate, horse, sheep, pig, goat, cow, cat, dog, primate, human or non-human primate; a plant, such as *Arabidopsis thaliana*, corn, sorghum, oat, wheat, rice, canola, or soybean; an algae, such as *Chlamydomonas reinhardtii*; a nematode such as *Caenorhabditis elegans*; an insect, such as *Drosophila melanogaster*, mosquito, fruit fly, honey bee or spider; a fish, such as zebrafish; a reptile; an amphibian, such as a frog or *Xenopus laevis*; a *Dictyostelium discoideum*; a fungi, such as *Pneumocystis carinii, Takifugu rubripes*, yeast, *Saccharamoyces cerevisiae*, or *Schizosaccharomyces pombe*; or a *Plasmodium falciparum*. Target nucleic acids can also be derived from a prokaryote such as a bacterium, *Escherichia coli*, staphylococci or *Mycoplasma pneumoniae*; an archaea; a virus such as Hepatitis C virus or human immunodeficiency virus; or a viroid. Target nucleic acids can be derived from a homogeneous culture or population of the above organisms or alternatively from a collection of several different organisms, for example, in a community or ecosystem.

Random fragmentation refers to the fragmentation of a polynucleotide molecule from a primary nucleic acid sample in a non-ordered fashion by enzymatic, chemical or mechanical means. Such fragmentation methods are known in the art and use standard methods (Sambrook and Russell, Molecular Cloning, A Laboratory Manual, third edition). In one embodiment, fragmentation can be accomplished using a process often referred to as tagmentation. Tagmentation uses a transposome complex and combines into a single step fragmentation and ligation to add universal adapters (Gunderson et al., WO 2016/130704). For the sake of clarity, generating smaller fragments of a larger piece of nucleic acid via specific PCR amplification of such smaller fragments is not equivalent to fragmenting the larger piece of nucleic acid because the larger piece of nucleic acid sequence remains in intact (i.e., is not fragmented by the PCR amplification). Moreover, random fragmentation is designed to produce fragments irrespective of the sequence identity or position of nucleotides comprising and/or surrounding the break. More particularly, the random fragmentation is by mechanical means such as nebulization or sonication to produce fragments of about 50 base pairs in length to about 1500 base pairs in length, still more particularly 50-700 base pairs in length, yet more particularly 50-400 base pairs in length. Most particularly, the method is used to generate smaller fragments of from 50-150 base pairs in length.

Fragmentation of polynucleotide molecules by mechanical means (nebulization, sonication and Hydroshear, for example) results in fragments with a heterogeneous mix of blunt and 3'- and 5'-overhanging ends. It is therefore desirable to repair the fragment ends using methods or kits (such as the Lucigen DNA terminator End Repair Kit) known in the art to generate ends that are optimal for insertion, for example, into blunt sites of cloning vectors. In a particular embodiment, the fragment ends of the population of nucleic acids are blunt ended. More particularly, the fragment ends are blunt ended and phosphorylated. The phosphate moiety can be introduced via enzymatic treatment, for example, using polynucleotide kinase.

A population of target nucleic acids, or amplicons thereof, can have an average strand length that is desired or appropriate for a particular application of the methods or compositions set forth herein. For example, the average strand length can be less than about 100,000 nucleotides, 50,000 nucleotides, 10,000 nucleotides, 5,000 nucleotides, 1,000 nucleotides, 500 nucleotides, 100 nucleotides, or 50 nucleotides. Alternatively, or additionally, the average strand length can be greater than about 10 nucleotides, 50 nucleotides, 100 nucleotides, 500 nucleotides, 1,000 nucleotides, 5,000 nucleotides, 10,000 nucleotides, 50,000 nucleotides, or 100,000 nucleotides. The average strand length for population of target nucleic acids, or amplicons thereof, can be in a range between a maximum and minimum value set forth above. It will be understood that amplicons generated at an amplification site (or otherwise made or used herein) can have an average strand length that is in a range between an upper and lower limit selected from those exemplified above.

In some cases, a population of target nucleic acids can be produced under conditions or otherwise configured to have a maximum length for its members. For example, the maximum length for the members that are used in one or more steps of a method set forth herein or that are present in a particular composition can be less than 100,000 nucleotides, less than 50,000 nucleotides, less than 10,000 nucleotides, less than 5,000 nucleotides, less than 1,000 nucleotides, less than 500 nucleotides, less than 100 nucleotides, or less than 50 nucleotides. Alternatively, or additionally, a population of target nucleic acids, or amplicons thereof, can be produced under conditions or otherwise configured to have a minimum length for its members. For example, the minimum length for the members that are used in one or more steps of a method set forth herein or that are present in a particular composition can be more than 10 nucleotides, more than 50 nucleotides, more than 100 nucleotides, more than 500 nucleotides, more than 1,000 nucleotides, more than 5,000 nucleotides, more than 10,000 nucleotides, more than 50,000 nucleotides, or more than 100,000 nucleotides. The maximum and minimum strand length for target nucleic acids in a population can be in a range between a maximum and minimum value set forth above. It will be understood that amplicons generated at an amplification site (or otherwise made or used herein) can have maximum and/or minimum strand lengths in a range between the upper and lower limits exemplified above.

In particular embodiments, the target nucleic acids are sized relative to the area of the amplification sites, for example, to facilitate exclusion amplification. For example, the area for each of the sites of an array can be greater than the diameter of the excluded volume of the target nucleic acids in order to achieve exclusion amplification. Taking, for example, embodiments that use an array of features on a surface, the area for each of the features can be greater than the diameter of the excluded volume of the target nucleic acids that are transported to the amplification sites. The excluded volume for a target nucleic acid and its diameter can be determined, for example, from the length of the target nucleic acid. Methods for determining the excluded volume of nucleic acids and the diameter of the excluded volume are described, for example, in U.S. Pat. No. 7,785,790; Rybenkov et al., Proc. Natl. Acad. Sci. U.S.A. 90: 5307-5311 (1993); Zimmerman et al., J. Mol. Biol. 222:599-620 (1991); or Sobel et al., Biopolymers 31:1559-1564 (1991).

In a particular embodiment, the target fragment sequences are prepared with single overhanging nucleotides by, for example, activity of certain types of DNA polymerase such as Taq polymerase or Klenow exo minus polymerase which has a non-template-dependent terminal transferase activity that adds a single deoxynucleotide, for example, deoxyadenosine (A) to the 3' ends of a DNA molecule, for example, a PCR product. Such enzymes can be used to add a single nucleotide 'A' to the blunt ended 3' terminus of each strand of the double-stranded target fragments. Thus, an 'A' could be added to the 3' terminus of each end repaired strand of the double-stranded target fragments by reaction with Taq or Klenow exo minus polymerase, while the universal adapter polynucleotide construct could be a T-construct with a compatible 'T' overhang present on the 3' terminus of each region of double stranded nucleic acid of the universal adapter. This end modification also prevents self-ligation of both vector and target such that there is a bias towards formation of the combined ligated adaptor-target-adaptor molecules.

In some cases, the target nucleic acids that are derived from such sources can be amplified prior to use in a method or composition herein. Any of a variety of known amplification techniques can be used including, but not limited to, polymerase chain reaction (PCR), rolling circle amplification (RCA), multiple displacement amplification (MDA), or random prime amplification (RPA). It will be understood that amplification of target nucleic acids prior to use in a method or composition set forth herein is optional. As such, target nucleic acids will not be amplified prior to use in some embodiments of the methods and compositions set forth herein. Target nucleic acids can optionally be derived from synthetic libraries. Synthetic nucleic acids can have native DNA or RNA compositions or can be analogs thereof.

Universal Adapters

A target nucleic acid used in a method or composition described herein includes a universal adapter attached to each end. Methods for attaching universal adapter to each end of a target nucleic acid used in a method described herein are known to the person skilled in the art. The attachment can be through standard library preparation techniques using ligation (Chesney et al. U.S. Pat. Pub. No. 2018/0305753 A1), or through tagmentation using transposase complexes (Gunderson et al., WO 2016/130704).

In one embodiment, double-stranded target nucleic acids from a sample, e.g., a fragmented sample, are treated by first ligating identical universal adaptor molecules ('mismatched adaptors', the general features of which are defined below, and further described in Gormley et al., U.S. Pat. No. 7,741,463, and Bignell et al., U.S. Pat. No. 8,053,192) to the 5' and 3' ends of the double-stranded target nucleic acids (which may be of known, partially known or unknown sequence). In one embodiment, the universal adaptor includes the universal capture binding sequences necessary for immobilizing the target nucleic acids on an array for subsequent sequencing. In another embodiment, a PCR step is used to further modify the universal adapter present at each end of target nucleic acids prior to immobilizing and sequencing. For instance, an initial primer extension reaction is carried out using a universal primer binding site in which extension products complementary to both strands of each individual target nucleic acid are formed and add a universal capture binding sequence. The resulting primer extension products, and optionally amplified copies thereof, collectively provide a library of modified target nucleic acids that can be immobilized and then sequenced. The term library refers to the collection of target nucleic acids containing known common sequences at their 3' and 5' ends, and may also be referred to as a 3' and 5' modified library. The 3' ends, and optionally the 5' ends, of the universal adapters attached to the target nucleic acids can include a homogeneous population or a heterogeneous population of universal capture binding sequences described herein.

The universal adapters used in the method of the disclosure are referred to as 'mismatched' adaptors because, as will be explained in detail herein, the adaptors include a region of sequence mismatch, i.e., they are not formed by annealing of fully complementary polynucleotide strands.

Mismatched adaptors for use herein are formed by annealing of two partially complementary polynucleotide strands to provide, when the two strands are annealed, at least one double-stranded region, also referred to as a region of double stranded nucleic acid, and at least one unmatched single-stranded region, also referred to as a region of single-stranded non-complementary nucleic acid strands.

The 'double-stranded region' of the universal adapter is a short double-stranded region, typically including 5 or more consecutive base pairs, formed by annealing of the two partially complementary polynucleotide strands. This term refers to a double-stranded region of nucleic acid in which the two strands are annealed and does not imply any particular structural conformation. As used herein, the term "double stranded," when used in reference to a nucleic acid molecule, means that substantially all of the nucleotides in the nucleic acid molecule are hydrogen bonded to a complementary nucleotide. A partially double stranded nucleic acid can have at least 10%, 25%, 50%, 60%, 70%, 80%, 90% or 95% of its nucleotides hydrogen bonded to a complementary nucleotide.

It is generally advantageous for the double-stranded region to be as short as possible without loss of function. In this context, 'function' refers to the ability of the double-stranded region to form a stable duplex under standard reaction conditions for an enzyme-catalyzed nucleic acid ligation reaction, which will be well known to the skilled reader (e.g. incubation at a temperature in the range of 4° C. to 25° C. in a ligation buffer appropriate for the enzyme), such that the two strands forming the universal adapter remain partially annealed during ligation of the universal adapter to a target molecule. It is not absolutely necessary for the double-stranded region to be stable under the conditions typically used in the annealing steps of primer extension or PCR reactions.

The double-stranded region of the universal adapters is typically identical in all universal adapters used in a ligation. Because universal adapters are ligated to both ends of each target molecule, the modified target nucleic acid will be flanked by complementary sequences derived from the double-stranded region of the universal adapters. The longer the double-stranded region, and hence the complementary sequences derived therefrom in the modified target nucleic acid constructs, the greater the possibility that the modified target nucleic acid construct is able to fold back and base-pair to itself in these regions of internal self-complementarity under the annealing conditions used in primer extension and/or PCR. It is, therefore, generally preferred for the double-stranded region to be 20 or less, 15 or less, or 10 or less base pairs in length in order to reduce this effect. The stability of the double-stranded region may be increased, and hence its length potentially reduced, by the inclusion of non-natural nucleotides which exhibit stronger base-pairing than standard Watson-Crick base pairs.

In one embodiment, the two strands of the universal adapter are 100% complementary in the double-stranded region. It will be appreciated that one or more nucleotide mismatches may be tolerated within the double-stranded region, provided that the two strands are capable of forming a stable duplex under standard ligation conditions.

Universal adaptors for use herein will generally include a double-stranded region forming the 'ligatable' end of the adaptor, e.g., the end that is joined to a double-stranded target nucleic acid in the ligation reaction. The ligatable end of the universal adaptor may be blunt or, in other embodiments, short 5' or 3' overhangs of one or more nucleotides may be present to facilitate/promote ligation. The 5' terminal nucleotide at the ligatable end of the universal adapter is typically phosphorylated to enable phosphodiester linkage to a 3' hydroxyl group on the target polynucleotide.

The term 'unmatched region' refers to a region of the universal adaptor, the region of single-stranded non-complementary nucleic acid strands, wherein the sequences of the two polynucleotide strands forming the universal adaptor exhibit a degree of non-complementarity such that the two strands are not capable of fully annealing to each other under standard annealing conditions for a primer extension or PCR reaction. The unmatched region(s) may exhibit some degree of annealing under standard reaction conditions for an enzyme-catalyzed ligation reaction, provided that the two strands revert to single stranded form under annealing conditions in an amplification reaction.

It is to be understood that the 'unmatched region' is provided by different portions of the same two polynucleotide strands which form the double-stranded region(s). Mismatches in the adaptor construct can take the form of one strand being longer than the other, such that there is a single stranded region on one of the strands, or a sequence selected such that the two strands do not hybridize, and thus form a single stranded region on both strands. The mismatches may also take the form of 'bubbles', wherein both ends of the universal adapter construct(s) are capable of hybridizing to each other and forming a duplex, but the central region is not. The portion of the strand(s) forming the unmatched region are not annealed under conditions in which other portions of the same two strands are annealed to form one or more double-stranded regions. For avoidance of doubt it is to be understood that a single-stranded or single base overhang at the 3' end of a polynucleotide duplex that subsequently undergoes ligation to the target sequences does not constitute an 'unmatched region' in the context of this disclosure.

The lower limit on the length of the unmatched region will typically be determined by function, for example, the need to provide a suitable sequence for i) binding of a primer for primer extension, PCR and/or sequencing (for instance, binding of a primer to a universal primer binding site), or for ii) binding of a universal capture binding sequence to a capture sequence for immobilization of a modified target nucleic acid to a surface. Theoretically there is no upper limit on the length of the unmatched region, except that in general it is advantageous to minimize the overall length of the universal adapter, for example, in order to facilitate separation of unbound universal adapters from modified target nucleic acid constructs following the ligation step. Therefore, it is generally preferred that the unmatched region should be less than 50, or less than 40, or less than 30, or less than 25 consecutive nucleotides in length.

The region of single-stranded non-complementary nucleic acid strands includes at least one universal capture binding sequence at the 3' end (see FIG. 1B, universal capture binding sequence 150). The 3' end of a universal adapter includes a first universal capture binding sequence that will hybridize to a first capture sequence present on a capture nucleic acid. For instance, as shown in FIG. 2, a nucleic acid 200 of a first population of capture nucleic acids includes a first capture sequence 210. One strand of a modified target nucleic acid 230 that includes a first universal capture binding sequence 250 at the 3' end of a single strand is shown hybridized to the first capture sequence 210. It is the interaction between the first universal capture binding sequence 250 and the first capture sequence 210 that is altered to reduce affinity and encode a kinetic delay into target nucleic acids seeded in a well. Standard ExAmp methods use universal capture binding sequences and capture sequences that are completely complementary over the entire length of the capture sequence. The ExAmp methods described herein use universal capture binding sequences that include one or more mismatches, have a reduced length, or a combination thereof. The result of the mismatch(es) and/or reduced length is reduced affinity between the two sequences compared to the affinity of the two completely complementary full-length sequences. The reduced affinity causes a decrease in the amplification efficiency, where the resulting amplification efficiency is, in general, a function of the number of differences between the universal capture binding sequence and the capture sequence.

Optionally, the 5' end of a universal adapter includes a second universal capture binding sequence attached to each end of a target nucleic acid, where the second universal capture binding sequence will hybridize to a second capture sequence present on a capture nucleic acid. For instance, as shown in FIG. 1B, universal capture binding sequence 180. Thus, unless noted otherwise, the following discussion of how a universal capture binding sequence is tuned to reduce affinity applies to both 3' and 5' universal capture binding sequences.

The 3' end of a capture sequence serves as the initiation point for DNA synthesis by a DNA polymerase in the methods described herein. The skilled person will recognize that the nucleotide at the 3' end of a capture sequence and the corresponding nucleotide in the universal capture binding sequence should be complementary to preserve the ability of a DNA polymerase to initiate DNA synthesis.

A universal capture binding sequence can include one or more nucleotides that are not complementary to the capture sequence. In one embodiment, a universal capture binding sequence can include from 1 to 5 mismatched nucleotides (also referred to as non-complementary nucleotides), for instance, at least 1, at least 2, at least 3, at least 4, or 5 mismatched nucleotides compared to a capture sequence used in an amplification reaction described herein. A mismatched nucleotide can be a wobble mismatch or a true mismatch.

A wobble mismatch refers to a position where all four nucleotides are represented in the population of the universal capture binding sequence. For instance, if N is the wobble nucleotide in ACTNGC, then the population of the universal capture binding sequence will include ACTTGC, ACTAGC, ACTCGC, and ACTGGC, and 25% of the universal capture binding sequences in the population will be complementary to the corresponding nucleotide of the capture sequence. In one embodiment, a universal capture binding sequence can include from 1 to 5 wobble nucleotides, for instance, at least 1, at least 2, at least 3, at least 4, or 5 wobble nucleotides compared to a capture sequence used in an amplification reaction described herein. In one embodiment, the wobble nucleotides can be located anywhere throughout the universal capture binding sequence.

A true mismatch refers to a position where only three of the four nucleotides are represented at a particular position in the population of the universal capture binding sequence. For instance, if G is the location of the true mismatched nucleotide in ACTTGC, then the population of the universal capture binding sequence will include ACTTCC, ACTTTC, and ACTTAC, and none of the universal capture binding sequences in the population will be complementary to the corresponding nucleotide, a C in this example, of the capture sequence. In one embodiment, a universal capture binding sequence can include from 1 to 5 mismatched nucleotides, for instance, at least 1, at least 2, at least 3, at least 4, or 5 wobble nucleotides compared to a capture sequence used in an amplification reaction described herein. In one embodiment, the wobble nucleotides can be located anywhere throughout the universal capture binding sequence.

The skilled person will recognize that the use of a wobble mismatch or a true mismatch provides for greater control of altering the affinity of a universal capture binding sequence. The use of a universal capture binding sequence with only a single wobble nucleotide results in 25% of the universal capture binding sequences having complementarity at that position, greater affinity than the other 75%, and an expected higher amplification efficiency than the other 75%. The use of a universal capture binding sequence with only a single true mismatch nucleotide results in all of the universal capture binding sequences having no complementarity at that position, reduced affinity, and an expected reduced amplification efficiency.

In another embodiment, a universal capture binding sequence has a shortened length that results in an affinity that is less than the affinity between the full-length universal capture binding sequence and capture sequence. Capture sequences useful in standard amplification methods described herein typically have a length of from about 20 to about 30 nucleotides, though they can be longer or shorter if needed. A universal capture binding sequence useful in the methods described herein can have a length that is 1, 2, 3, 4, 5, 6, 7, 8, 9, 10, 11, or 12 nucleotides shorter than the capture sequence used in an amplification reaction described herein. In one embodiment, the length of the universal capture binding sequence is reduced by removal of nucleotides from the 3' end of the first universal capture binding sequence and/or from the 5' end of the second universal capture binding sequence.

An amplification reaction described herein can use a heterogeneous population of universal capture binding sequences (e.g., a plurality of different target nucleic acids can include a heterogeneous population of universal capture binding sequences present at the 3' ends and optionally present at the 5' ends). In one embodiment, the heterogeneous population includes individual universal capture binding sequences having mismatched nucleotides. In one embodiment, the universal capture binding sequences have 1, 2, 3, 4, or 5 mismatched nucleotides. The mismatched nucleotides can be wobble mismatches, true mismatches, or a combination thereof.

In one embodiment, the heterogeneous population includes individual universal capture binding sequences having a shortened length. In one embodiment, the heterogeneous population includes individual universal capture binding sequences having a length that is 1, 2, 3, 4, 5, 6, 7, 8, 9, 10, 11, or 12 nucleotides shorter than the capture sequence used in an amplification reaction described herein.

In one embodiment, the heterogeneous population includes individual universal capture binding sequences having a combination of one or more mismatched nucleotides and a shortened length. The number of mismatched nucleotides and the number of nucleotides missing from universal capture binding sequence can be present in any combination, e.g., the number of mismatched nucleotides and the number of missing nucleotides are independent.

The heterogeneous population can also include individual target nucleic acids having at the 3' ends, and optionally at the 5' ends, a universal capture binding sequence that has 100% complementarity with the capture sequence. The molar ratios of the different universal capture binding sequences in a heterogeneous population can be equal or altered. In those embodiments where the molar ratio is not equal, higher molar ratios of those universal capture binding sequences having a higher amplification efficiency are preferred. Accordingly, in those embodiments where the heterogeneous population includes a universal capture binding sequence having 100% complementarity with the capture sequence, the universal capture binding sequence having 100% complementarity can be present at a greater proportion than any other member of the heterogeneous population.

The region of single-stranded non-complementary nucleic acid strands typically also includes at least one universal primer binding site. A universal primer binding site is a universal sequence that can be used for amplification and/or sequencing of a target nucleic acid ligated to the universal adapter.

The region of single-stranded non-complementary nucleic acid strands can also include at least one index. An index can be used as a marker characteristic of the source of particular target nucleic acid on an array. Generally, the index is a synthetic sequence of nucleotides that is part of the universal adapter which is added to the target nucleic acids as part of the library preparation step. Accordingly, an index is a nucleic acid sequence which is attached to each of the target molecules of a particular sample, the presence of which is indicative of, or is used to identify, the sample or source from which the target molecules were isolated.

Preferably, the index may be up to 20 nucleotides in length, more preferably 1-10 nucleotides, and most preferably 4-8 nucleotides in length. For example, a four-nucleotide index gives a possibility of multiplexing 256 ($4^4$) samples on the same array, whereas a six base index enables 4,096 ($4^6$) samples to be processed on the same array.

In one embodiment, the universal capture binding sequence is part of the universal adapter when it is ligated to the double-stranded target fragments, and in another embodiment the universal primer extension binding site is added to the universal adapter after the universal adapter is ligated to the double-stranded target fragments. The addition can be accomplished using routine methods, including PCR-based methods.

The precise nucleotide sequence of the universal adapters is generally not material to the invention and may be selected by the user such that the desired sequence elements are ultimately included in the common sequences of the plurality of different modified target nucleic acids, for example, to provide for the universal capture binding sequences and binding sites for particular sets of universal amplification primers and/or sequencing primers. Additional sequence elements may be included, for example, to provide binding sites for sequencing primers which will ultimately be used in sequencing of target nucleic acids in the library, or products derived from amplification of the target nucleic acids in the library, for example on a solid support.

Although the precise nucleotide sequence of the universal adapter is generally non-limiting to the disclosure, the sequences of the individual strands in the unmatched region should be such that neither individual strand exhibits any internal self-complementarity which could lead to self-annealing, formation of hairpin structures, etc. under standard annealing conditions. Self-annealing of a strand in the unmatched region is to be avoided as it may prevent or reduce specific binding of an amplification primer to this strand.

The mismatched adaptors are preferably formed from two strands of DNA, but may include mixtures of natural and non-natural nucleotides (e.g. one or more ribonucleotides) linked by a mixture of phosphodiester and non-phosphodiester backbone linkages.

Ligation and Amplification

Ligation methods are known in the art and use standard methods. Such methods use ligase enzymes such as DNA ligase to effect or catalyze joining of the ends of the two polynucleotide strands of, in this case, the universal adapter and the double-stranded target nucleic acids, such that covalent linkages are formed. The universal adapter may contain a 5'-phosphate moiety to facilitate ligation to the 3'-OH present on the target fragment. The double-stranded target nucleic acid contains a 5'-phosphate moiety, either residual from the shearing process, or added using an enzymatic treatment step, and has been end repaired, and optionally extended by an overhanging base or bases, to give a 3'-OH suitable for ligation. In this context, joining means covalent linkage of polynucleotide strands which were not previously covalently linked. In a particular aspect of the disclosure, such joining takes place by formation of a phosphodiester linkage between the two polynucleotide strands, but other means of covalent linkage (e.g. non-phosphodiester backbone linkages) may be used.

As discussed herein, in one embodiment universal adaptors used in the ligation are complete and include a universal capture binding sequence and other universal sequences, e.g., a universal primer binding site and an index sequence. The resulting plurality of target nucleic acids can be used to prepare immobilized samples for sequencing.

Also, as discussed herein, in one embodiment universal adaptors used in the ligation include a universal primer binding site and an index sequence, and do not include a universal capture binding sequence. The resulting plurality of modified target nucleic acids can be further modified to include specific sequences, such as a universal capture binding sequence. Methods for addition of specific sequences, such as a universal capture binding sequence, to universal primers that are ligated to double-stranded target fragments include PCR based methods, and are known in the art and are described in, for instance, Bignell et al. (U.S. Pat. No. 8,053,192) and Gunderson et al. (WO2016/130704).

In those embodiments where a universal adapter is modified, an amplification reaction is prepared. The contents of an amplification reaction are known by one skilled in the art and include appropriate substrates (such as dNTPs), enzymes (e.g. a DNA polymerase) and buffer components required for an amplification reaction. Generally, amplification reactions require at least two amplification primers, often denoted 'forward' and 'reverse' primers (primer oligonucleotides) that are capable of annealing specifically to a part of the polynucleotide sequence to be amplified, e.g., a target nucleic acid, under conditions encountered in the primer annealing step of each cycle of an amplification reaction. It will be appreciated that if the primers contain any nucleotide sequence which does not anneal to the modified target nucleic acids in the first amplification cycle then this sequence may be copied into the amplification products. For instance, the use of primers having universal capture binding sequences, i.e., sequences that do not anneal to the modified target nucleic acids, the universal capture binding sequences will be incorporated into the resulting amplicon.

Amplification primers are generally single stranded polynucleotide structures. They may also contain a mixture of natural and non-natural bases and also natural and non-natural backbone linkages, provided that any non-natural modifications do not preclude function as a primer—that being defined as the ability to anneal to a template polynucleotide strand during conditions of the amplification reaction and to act as an initiation point for synthesis of a new polynucleotide strand complementary to the template strand. Primers may additionally include non-nucleotide chemical modifications, for example phosphorothioates to increase exonuclease resistance, again provided such that modifications do not prevent primer function.

Preparation of Immobilized Samples for Sequencing

A method of the present disclosure can include reacting an amplification reagent (an array of amplification sites and a plurality of different modified target nucleic acids) to produce a plurality of amplification sites that each includes a clonal population of amplicons from an individual target nucleic acid that has seeded the site. In standard reactions, exclusion amplification occurs due to the relatively slow rate of target nucleic acid seeding (e.g. relatively slow diffusion or transport) vs. the relatively rapid rate at which amplification occurs to fill the site with copies of the nucleic acid seed. In the methods described herein, exclusion amplification can occur due to a kinetic delay in the formation of a first copy of a target nucleic acid that has seeded a site vs. the relatively rapid rate at which subsequent copies are made to fill the site. For instance, an individual site may have been seeded with several different target nucleic acids, each having a different universal capture binding sequence (e.g., a plurality of different modified target nucleic acids includes a heterogeneous population of universal capture binding sequences). However, first copy formation for any given target nucleic acid is expected to depend on the amplification efficiency of its universal capture binding sequence, such that the average rate of first copy formation is relatively slow compared to the rate at which subsequent copies are generated. In this case, although an individual site may have been seeded with several different target nucleic acids, only one will begin amplification first, and exclusion amplification will typically allow only that target nucleic acid to fill the amplification site. More specifically, once a first target nucleic acid begins amplification, the site will rapidly fill to capacity with its copies, thereby preventing copies of a second target nucleic acid from being made at the site.

In some embodiments, apparent clonality can be achieved even if an amplification site is not filled to capacity prior to a second target nucleic acid beginning amplification at the site. Under some conditions, amplification of a first target nucleic acid can proceed to a point that a sufficient number of copies are made to effectively outcompete or overwhelm production of copies from a second target nucleic acid that is transported to the site. For example, in an embodiment that uses a bridge amplification process on a circular feature that is smaller than 500 nm in diameter, it has been determined that after 14 cycles of exponential amplification for a first target nucleic acid, contamination from a second target nucleic acid at the same site will produce an insufficient number of contaminating amplicons to adversely impact sequencing-by-synthesis analysis on an Illumina sequencing platform.

Amplification sites in an array need not be entirely clonal in all embodiments. Rather, for some applications, an individual amplification site can be predominantly populated with amplicons from a first target nucleic acid and can also have a low level of contaminating amplicons from a second target nucleic acid. An array can have one or more amplification sites that have a low level of contaminating amplicons so long as the level of contamination does not have an unacceptable impact on a subsequent use of the array. For example, when the array is to be used in a detection application, an acceptable level of contamination would be a level that does not impact signal to noise or resolution of the detection technique in an unacceptable way. Accordingly, apparent clonality will generally be relevant to a particular use or application of an array made by the methods set forth herein. Exemplary levels of contamination that can be acceptable at an individual amplification site for particular applications include, but are not limited to, at most 0.1%, 0.5%, 1%, 5%, 10% or 25% contaminating amplicons. An array can include one or more amplification sites having these exemplary levels of contaminating amplicons. For example, up to 5%, 10%, 25%, 50%, 75%, or even 100% of the amplification sites in an array can have some contaminating amplicons.

Although the use of differentially active primers to cause different rates of first amplicon and subsequent amplicon formation has been exemplified above for an embodiment where target nucleic acids are present at amplification sites prior to amplification, the method can also be carried out under conditions wherein the target nucleic acids are transported (e.g. via diffusion) to the amplification sites as amplification is occurring. Thus, exclusion amplification can exploit both a relatively slow transport rate and a relatively slow production of first amplicon relative to subsequent amplicon formation. Thus, an amplification reaction set forth herein can be carried out such that target nucleic acids are transported from solution to amplification sites simultaneously with (i) the producing of a first amplicon, and (ii) the producing of the subsequent amplicons at other sites of the array. In particular embodiments, the average rate at which the subsequent amplicons are generated at the amplification sites can exceed the average rate at which the target nucleic acids are transported from the solution to the amplification sites. In some cases, a sufficient number of amplicons can be generated from a single target nucleic acid at an individual amplification site to fill the capacity of the respective amplification site. The rate at which amplicons are generated to fill the capacity of respective amplification sites can, for example, exceed the rate at which the individual target nucleic acids are transported from the solution to the amplification sites.

An amplification reagent that is used in a method set forth herein is preferably capable of rapidly making copies of target nucleic acids at amplification sites. Typically, an amplification reagent used in a method of the present disclosure will include a polymerase and nucleotide triphosphates (NTPs). Any of a variety of polymerases known in the art can be used, but in some embodiments, it may be preferable to use a polymerase that is exonuclease negative. The NTPs can be deoxyribonucleotide triphosphates (dNTPs) for embodiments where DNA copies are made. Typically, the four native species, dATP, dTTP, dGTP and dCTP, will be present in a DNA amplification reagent; however, analogs can be used if desired. The NTPs can be ribonucleotide triphosphates (rNTPs) for embodiments where RNA copies are made. Typically, the four native species, rATP, rUTP, rGTP and rCTP, will be present in an RNA amplification reagent; however, analogs can be used if desired.

An amplification reagent can include further components that facilitate amplicon formation and, in some cases, increase the rate of amplicon formation. An example is a recombinase loading protein. Recombinase can facilitate amplicon formation by allowing repeated invasion/extension. More specifically, recombinase can facilitate invasion of a target nucleic acid by the polymerase and extension of a primer by the polymerase using the target nucleic acid as a template for amplicon formation. This process can be repeated as a chain reaction where amplicons produced from each round of invasion/extension serve as templates in a subsequent round. The process can occur more rapidly than standard PCR since a denaturation cycle (e.g. via heating or chemical denaturation) is not required. As such, recombinase-facilitated amplification can be carried out isothermally. It is generally desirable to include ATP, or other nucleotides (or in some cases non-hydrolyzable analogs thereof) in a recombinase-facilitated amplification reagent to facilitate amplification. A mixture of recombinase, single stranded binding (SSB) protein, and accessory protein is particularly useful. Exemplary formulations for recombinase-facilitated amplification include those sold commercially as TwistAmp kits by TwistDx (Cambridge, UK). Useful components of recombinase-facilitated amplification reagent and reaction conditions are set forth in U.S. Pat. Nos. 5,223,414 and 7,399,590, each of which is incorporated herein by reference.

Another example of a component that can be included in an amplification reagent to facilitate amplicon formation and in some cases to increase the rate of amplicon formation is a helicase. Helicase can facilitate amplicon formation by allowing a chain reaction of amplicon formation. The process can occur more rapidly than standard PCR since a denaturation cycle (e.g. via heating or chemical denaturation) is not required. As such, helicase-facilitated amplification can be carried out isothermally. A mixture of helicase and single stranded binding (SSB) protein is particularly useful as SSB can further facilitate amplification. Exemplary formulations for helicase-facilitated amplification include those sold commercially as IsoAmp kits from Biohelix (Beverly, Mass.). Further, examples of useful formulations that include a helicase protein are described in U.S. Pat. Nos. 7,399,590 and 7,829,284, each of which is incorporated herein by reference.

Yet another example of a component that can be included in an amplification reagent to facilitate amplicon formation and in some cases increase the rate of amplicon formation is an origin binding protein.

The presence of molecular crowding reagents in the solution can be used to aid exclusion amplification. Examples of useful molecular crowding reagents include, but are not limited to, polyethylene glycol (PEG), Ficoll®, dextran, or polyvinyl alcohol. Exemplary molecular crowding reagents and formulations are set forth in U.S. Pat. No. 7,399,590.

The rate at which an amplification reaction occurs can be increased by increasing the concentration or amount of one or more of the active components of an amplification reaction. For example, the amount or concentration of polymerase, nucleotide triphosphates, primers, recombinase, helicase or SSB can be increased to increase the amplification rate. In some cases, the one or more active components of an amplification reaction that are increased in amount or concentration (or otherwise manipulated in a method set forth herein) are non-nucleic acid components of the amplification reaction.

Amplification rate can also be increased in a method set forth herein by adjusting the temperature. For example, the rate of amplification at one or more amplification sites can be increased by increasing the temperature at the site(s) up to a maximum temperature where reaction rate declines due to denaturation or other adverse events. Optimal or desired temperatures can be determined from known properties of the amplification components in use or empirically for a given amplification reaction mixture. Such adjustments can be made based on a priori predictions of primer melting temperature (Tm) or empirically.

The rate at which an amplification reaction occurs can be increased by increasing the activity of one or more amplification reagent. For example, a cofactor that increases the extension rate of a polymerase can be added to a reaction where the polymerase is in use. In some embodiments, metal cofactors such as magnesium, zinc or manganese can be added to a polymerase reaction or betaine can be added.

In some embodiments of the methods set forth herein, it is desirable to use a population of target nucleic acids that is double-stranded. It has been observed that amplicon formation at an array of sites under exclusion amplification conditions is efficient for double-stranded target nucleic acids. For example, a plurality of amplification sites having clonal populations of amplicons can be more efficiently produced from double-stranded target nucleic acids (compared to single-stranded target nucleic acids at the same concentration) in the presence of recombinase and single-stranded binding protein. Nevertheless, it will be understood that single-stranded target nucleic acids can be used in some embodiments of the methods set forth herein.

A method set forth herein can use any of a variety of amplification techniques. Exemplary techniques that can be used include, but are not limited to, polymerase chain reaction (PCR), rolling circle amplification (RCA), multiple displacement amplification (MDA), or random prime amplification (RPA). In some embodiments the amplification can be carried out in solution, for example, when the amplification sites are capable of containing amplicons in a volume having a desired capacity. Preferably, an amplification technique used under conditions of exclusion amplification in a method of the present disclosure will be carried out on solid phase. For example, one or more primers used for amplification can be attached to a solid phase at the amplification site. In PCR embodiments, one or both of the primers used for amplification can be attached to a solid phase. Formats that utilize two species of primer attached to the surface are often referred to as bridge amplification because double stranded amplicons form a bridge-like structure between the two surface-attached primers that flank the template sequence that has been copied. Exemplary reagents and conditions that can be used for bridge amplification are described, for example, in U.S. Pat. No. 5,641,658; U.S. Pat. Pub. No. 2002/0055100; U.S. Pat. No. 7,115,400; U.S. Pat. Pub. No. 2004/0096853; U.S. Pat. Pub. No. 2004/0002090; U.S. Pat. Pub. No. 2007/0128624; and U.S. Pat. Pub. No. 2008/0009420. Solid-phase PCR amplification can also be carried out with one of the amplification primers attached to a solid support and the second primer in solution. An exemplary format that uses a combination of a surface attached primer and soluble primer is emulsion PCR as described, for example, in Dressman et al., Proc. Natl. Acad. Sci. USA 100:8817-8822 (2003), WO 05/010145, or U.S. Pat. Pub. Nos. 2005/0130173 or 2005/0064460. Emulsion PCR is illustrative of the format and it will be understood that for purposes of the methods set forth herein the use of an emulsion is optional and indeed for several embodiments an emulsion is not used. The described PCR techniques can be modified for non-cyclic amplification (e.g. isothermal amplification) using components exemplified elsewhere herein for facilitating or increasing the rate of amplification. Accordingly, the described PCR techniques can be used under exclusion amplification conditions.

RCA techniques can be modified for use in a method of the present disclosure. Exemplary components that can be used in an RCA reaction and principles by which RCA produces amplicons are described, for example, in Lizardi et al., Nat. Genet. 19:225-232 (1998) and US 2007/0099208 A1. Primers used for RCA can be in solution or attached to a solid support surface at an amplification site. The RCA techniques exemplified in the above references can be modified in accordance with teaching herein, for example, to increase the rate of amplification to suit particular applications. Thus, RCA techniques can be used under exclusion amplification conditions.

MDA techniques can be modified for use in a method of the present disclosure. Some basic principles and useful conditions for MDA are described, for example, in Dean et al., Proc Natl. Acad. Sci. USA 99:5261-66 (2002); Lage et al., Genome Research 13:294-307 (2003); Walker et al., Molecular Methods for Virus Detection, Academic Press, Inc., 1995; Walker et al., Nucl. Acids Res. 20:1691-96 (1992); U.S. Pat. Nos. 5,455,166; 5,130,238; and 6,214,587. Primers used for MDA can be in solution or attached to a solid support surface at an amplification site. The MDA techniques exemplified in the above references can be modified in accordance with teaching herein, for example, to increase the rate of amplification to suit particular applications. Accordingly, MDA techniques can be used under exclusion amplification conditions.

In particular embodiments a combination of the described amplification techniques can be used to make an array under exclusion amplification conditions. For example, RCA and MDA can be used in a combination wherein RCA is used to generate a concatemeric amplicon in solution (e.g. using solution-phase primers). The amplicon can then be used as a template for MDA using primers that are attached to a solid support surface at an amplification site. In this example, amplicons produced after the combined RCA and MDA steps will be attached to the surface of the amplification site.

As exemplified with respect to several of the embodiments above, a method of the present disclosure need not use a cyclical amplification technique. For example, amplification of target nucleic acids can be carried out at amplification sites absent a denaturation cycle. Exemplary denaturation cycles include introduction of chemical denaturants to an amplification reaction and/or increasing the temperature of an amplification reaction. Thus, amplifying of the target nucleic acids need not include a step of replacing the amplification solution with a chemical reagent that denatures the target nucleic acids and the amplicons. Similarly, amplifying of the target nucleic acids need not include heating the solution to a temperature that denatures the target nucleic acids and the amplicons. Accordingly, amplifying of target nucleic acids at amplification sites can be carried out isothermally for the duration of a method set forth herein. Indeed, an amplification method set forth herein can occur without one or more cyclic manipulations that are carried out for some amplification techniques under standard conditions. Furthermore, in some standard solid phase amplification techniques a wash is carried out after target nucleic acids are loaded onto a substrate and before amplification is initiated. However, in embodiments of the present methods, a wash step need not be carried out between transport of target nucleic acids to reaction sites and amplification of the target nucleic acids at the amplification sites. Instead transport (e.g. via diffusion) and amplification are allowed to occur simultaneously to provide for exclusion amplification.

In some embodiments, it may be desirable to repeat an amplification cycle that occurs under exclusion amplification conditions. Thus, although copies of a target nucleic acid can be made at an individual amplification site without cyclic manipulations, an array of amplification sites can be treated cyclically to increase the number of sites that contain amplicons after each cycle. In particular embodiments, the amplification conditions can be modified from one cycle to the next. For example, one or more of the conditions set forth above for altering the rate of transport or altering the rate of amplification can be adjusted between cycles. As such, the rate of transport can be increased from cycle to cycle, the rate of transport can be decreased from cycle to cycle, the rate of amplification can be increased from cycle to cycle, or the rate of amplification can be decreased from cycle to cycle.

Compositions

During or following an amplification clustering method described herein, different compositions can result. In one embodiment, a composition includes an array of amplification sites. Each site includes first and second capture nucleic acids that include first and second capture sequences, respectively, where the first and second capture nucleic acids are bound to the surface of the sites. The different sites of the array include target nucleic acids hybridized to the first capture sequence of the first capture nucleic acid. The target nucleic acids at the different sites each include at the 3' end a universal capture binding sequence that is hybridized to the capture sequence. Universal capture binding sequences are present that have less affinity for the capture sequence than a universal capture binding sequence having 100% complementarity with the first capture sequence. In one embodiment, different universal capture binding sequences are present at each site, e.g., a first heterogeneous population of universal capture binding sequences are present. The first heterogeneous population can include at least 2, at least 3, at least 4, at least 5, at least 6, at least 7, or at least 8 different universal capture binding sequences.

In one embodiment, the first universal capture binding sequence includes 1 to 5 nucleotides that are non-complementary to the first capture sequence. The composition can include some target nucleic acids having a universal capture binding sequence with 100% complementarity to the first capture sequence. In one embodiment, the members of the first heterogeneous population having 100% complementarity with the first capture sequence are present at a greater number than the other members of the first heterogeneous population. The first heterogeneous population can also include individual first universal capture binding sequences having a length that is less than the length of the first capture sequence, such as a length that is from 1 to 12 nucleotides less than the length of the first capture sequence. Individual members of the first heterogeneous population can have both a length that is less than the length of the first capture sequence and include either 1 to 5 nucleotides that are non-complementary to the sequence of the first capture sequence, or 100% complementarity with the sequence of the first capture sequence.

The 5' end can optionally include a second universal capture binding sequence having a complement that has less affinity for the second capture sequence than a second universal capture binding sequence having a complement with 100% complementarity to the second capture sequence. In one embodiment, the complement of the second universal capture binding sequence includes 1 to 5 nucleotides that are non-complementary to the second capture sequence. The composition can include some target nucleic acids having a second universal capture binding sequence with a complement having 100% complementarity to the second capture sequence. In one embodiment, different second universal capture binding sequences are present at each site, e.g., a second heterogeneous population of second universal capture binding sequences are present. The second heterogeneous population can include at least 2, at least 3, at least 4, at least 5, at least 6, at least 7, or at least 8 different second universal capture binding sequences. In one embodiment, the members of a second heterogeneous population with a complement having 100% complementarity to the second capture sequence are present at a greater number than the other members of the second heterogeneous population. The second heterogeneous population of universal capture binding sequences at the 5' end can also include individual second universal capture binding sequences having a length that is less than the length of the second capture sequence, such as a length that is from 1 to 12 nucleotides less than the length of the second capture sequence. Individual members of the second heterogeneous population can have both a length that is less than the length of the second capture sequence and include a complement having 1 to 5 nucleotides that are non-complementary to the sequence of the second capture sequence, or 100% complementarity with the sequence of the second capture sequence.

Another composition that can result includes a solution that includes different double-stranded target nucleic acids from a single sample or source, e.g., a library, where each target nucleic acid includes a universal adapter attached at each end. The universal adapters include a universal capture binding sequence, and the universal capture binding sequence is a heterogeneous population. The heterogeneous population can include at least 2, at least 3, at least 4, at least 5, at least 6, at least 7, or at least 8 different universal capture binding sequences.

Use in Sequencing/Methods of Sequencing

An array of the present disclosure, for example, having been produced by a method set forth herein and including amplified target nucleic acids at amplification sites, can be used for any of a variety of applications. A particularly useful application is nucleic acid sequencing. One example is sequencing-by-synthesis (SBS). In SBS, extension of a nucleic acid primer along a nucleic acid template (e.g., a target nucleic acid or amplicon thereof) is monitored to determine the sequence of nucleotides in the template. The underlying chemical process can be polymerization (e.g., as catalyzed by a polymerase enzyme). In a particular polymerase-based SBS embodiment, fluorescently labeled nucleotides are added to a primer (thereby extending the primer) in a template dependent fashion such that detection of the order and type of nucleotides added to the primer can be used to determine the sequence of the template. A plurality of different templates at different sites of an array set forth herein can be subjected to an SBS technique under conditions where events occurring for different templates can be distinguished due to their location in the array.

Flow cells provide a convenient format for housing an array that is produced by the methods of the present disclosure and that is subjected to an SBS or other detection technique that involves repeated delivery of reagents in cycles. For example, to initiate a first SBS cycle, one or more labeled nucleotides, DNA polymerase, etc., can be flowed into/through a flow cell that houses an array of nucleic acid templates. Those sites of an array where primer extension causes a labeled nucleotide to be incorporated can be detected. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with an array produced by the methods of the present disclosure are described, for example, in Bentley et al., Nature 456: 53-59 (2008), WO 04/018497; U.S. Pat. No. 7,057,026; WO 91/06678; WO 07/123,744; U.S. Pat. Nos. 7,329,492; 7,211, 414; 7,315,019; 7,405,281, and 8,343,746.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., Analytical Biochemistry 242(1), 84-9 (1996); Ronaghi, Genome Res. 11(1), 3-11 (2001); Ronaghi et al. Science 281(5375), 363 (1998); U.S. Pat. Nos. 6,210, 891; 6,258,568 and 6,274,320). In pyrosequencing, released PPi can be detected by being immediately converted to adenosine triphosphate (ATP) by ATP sulfurylase, and the level of ATP generated can be detected via luciferase-produced photons. Thus, the sequencing reaction can be monitored via a luminescence detection system. Excitation radiation sources used for fluorescence-based detection systems are not necessary for pyrosequencing procedures. Useful fluidic systems, detectors and procedures that can be used for application of pyrosequencing to arrays of the present disclosure are described, for example, in WIPO Published Pat. App. 2012/058096, US 2005/0191698 A1, U.S. Pat. Nos. 7,595,883, and 7,244,559.

Sequencing-by-ligation reactions are also useful including, for example, those described in Shendure et al. Science 309:1728-1732 (2005); U.S. Pat. Nos. 5,599,675; and 5,750, 341. Some embodiments can include sequencing-by-hybridization procedures as described, for example, in Bains et al., Journal of Theoretical Biology 135(3), 303-7 (1988); Drmanac et al., Nature Biotechnology 16, 54-58 (1998); Fodor et al., Science 251(4995), 767-773 (1995); and WO 1989/10977. In both sequencing-by-ligation and sequencing-by-hybridization procedures, template nucleic acids (e.g., a target nucleic acid or amplicons thereof) that are present at sites of an array are subjected to repeated cycles of oligonucleotide delivery and detection. Fluidic systems for SBS methods as set forth herein or in references cited herein can be readily adapted for delivery of reagents for sequencing-by-ligation or sequencing-by-hybridization procedures. Typically, the oligonucleotides are fluorescently labeled and can be detected using fluorescence detectors similar to those described with regard to SBS procedures herein or in references cited herein.

Some embodiments can use methods involving the real-time monitoring of DNA polymerase activity. For example, nucleotide incorporations can be detected through fluorescence resonance energy transfer (FRET) interactions between a fluorophore-bearing polymerase and $\gamma$-phosphate-labeled nucleotides, or with zeromode waveguides (ZMWs). Techniques and reagents for FRET-based sequencing are described, for example, in Levene et al. Science 299, 682-686 (2003); Lundquist et al. Opt. Lett. 33, 1026-1028 (2008); Korlach et al. Proc. Natl. Acad. Sci. USA 105, 1176-1181 (2008).

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in US 2009/ 0026082 A1; US 2009/0127589 A1; US 2010/0137143 A1; or US 2010/0282617 A1. Methods set forth herein for amplifying target nucleic acids using exclusion amplification can be readily applied to substrates used for detecting protons. More specifically, methods set forth herein can be used to produce clonal populations of amplicons at the sites of the arrays that are used to detect protons.

A useful application for an array of the present disclosure, for example, having been produced by a method set forth herein, is gene expression analysis. Gene expression can be detected or quantified using RNA sequencing techniques, such as those referred to as digital RNA sequencing. RNA sequencing techniques can be carried out using sequencing methodologies known in the art such as those set forth above. Gene expression can also be detected or quantified using hybridization techniques carried out by direct hybridization to an array or using a multiplex assay, the products of which are detected on an array. An array of the present disclosure, for example, having been produced by a method set forth herein, can also be used to determine genotypes for a genomic DNA sample from one or more individual. Exemplary methods for array-based expression and genotyping analysis that can be carried out on an array of the present disclosure are described in U.S. Pat. Nos. 7,582,420; 6,890,741; 6,913,884 or 6,355,431 or US Pat. Pub. Nos. 2005/0053980 A1; 2009/0186349 A1 or US 2005/0181440 A1.

Another useful application for an array having been produced by a method set forth herein is single-cell sequencing. When combined with indexing methods single cell sequencing can be used in chromatin accessibility assays to produce profiles of active regulatory elements in thousands of single cells, and single cell whole genome libraries can be produced. Examples for single-cell sequencing that can be carried out on an array of the present disclosure are described in U.S. Published Patent Application 2018/0023119 A1, U.S. Provisional Applications Ser. Nos. 62/673,023 and 62/680,259.

An advantage of the methods set forth herein is that they provide for rapid and efficient creation of arrays from any of a variety of nucleic acid libraries. Accordingly, the present disclosure provides integrated systems capable of making an array using one or more of the methods set forth herein and further capable of detecting nucleic acids on the arrays using techniques known in the art such as those exemplified above. Thus, an integrated system of the present disclosure can include fluidic components capable of delivering amplification reagents to an array of amplification sites such as pumps, valves, reservoirs, fluidic lines and the like. A particularly useful fluidic component is a flow cell. A flow cell can be configured and/or used in an integrated system to create an array of the present disclosure and to detect the array. Exemplary flow cells are described, for example, in US 2010/0111768 A1 and U.S. Pat. No. 8,951,781. As exemplified for flow cells, one or more of the fluidic components of an integrated system can be used for an amplification method and for a detection method. Taking a nucleic acid sequencing embodiment as an example, one or more of the fluidic components of an integrated system can be used for an amplification method set forth herein and for the delivery of sequencing reagents in a sequencing method such as those exemplified above. Alternatively, an integrated system can include separate fluidic systems to carry out amplification methods and to carry out detection methods. Examples of integrated sequencing systems that are capable of creating arrays of nucleic acids and also determining the sequence of the nucleic acids include, without limitation, the MiSeq™, HiSeq™, NextSeq™, MiniSeq™, NovaSeq™ and iSeq™ platforms (Illumina, Inc., San Diego, Calif.) and devices described in U.S. Pat. No. 8,951,781. Such devices can be modified to make arrays using exclusion amplification in accordance with the guidance set forth herein.

A system capable of carrying out a method set forth herein need not be integrated with a detection device. Rather, a stand-alone system or a system integrated with other devices is also possible. Fluidic components similar to those exemplified above in the context of an integrated system can be used in such embodiments.

A system capable of carrying out a method set forth herein, whether integrated with detection capabilities or not, can include a system controller that is capable of executing a set of instructions to perform one or more steps of a method, technique or process set forth herein. For example, the instructions can direct the performance of steps for creating an array under exclusion amplification conditions. Optionally, the instructions can further direct the performance of steps for detecting nucleic acids using methods set forth previously herein. A useful system controller may include any processor-based or microprocessor-based system, including systems using microcontrollers, reduced instruction set computers (RISC), application specific integrated circuits (ASICs), field programmable gate array (FPGAs), logic circuits, and any other circuit or processor capable of executing functions described herein. A set of instructions for a system controller may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The software may be in various forms such as system software or application software. Further, the software may be in the form of a collection of separate programs, or a program module within a larger program or a portion of a program module. The software also may include modular programming in the form of object-oriented programming.

Several applications for arrays of the present disclosure have been exemplified above in the context of ensemble detection, wherein multiple amplicons present at each amplification site are detected together. In alternative embodiments, a single nucleic acid, whether a target nucleic acid or amplicon thereof, can be detected at each amplification site. For example, an amplification site can be configured to contain a single nucleic acid molecule having a target nucleotide sequence that is to be detected and a plurality of filler nucleic acids. In this example, the filler nucleic acids function to fill the capacity of the amplification site and they are not necessarily intended to be detected. The single molecule that is to be detected can be detected by a method that is capable of distinguishing the single molecule in the background of the filler nucleic acids. Any of a variety of single molecule detection techniques can be used including, for example, modifications of the ensemble detection techniques set forth above to detect the sites at increased gain or using more sensitive labels. Other examples of single molecule detection methods that can be used are set forth in U.S. 2011/0312529 A1; U.S. Pat. No. 9,279,154; and U.S. 2013/0085073 A1.

An array useful for single molecule nucleic acid detection can be created using one or more of the methods set forth herein with the following modifications. A plurality of different target nucleic acids can be configured to include both a target nucleotide sequence that is to be detected and one or more filler nucleotide sequences that are to be amplified to create filler amplicons. The plurality of different target nucleic acids can be included in an amplification reagent, such as those set forth elsewhere herein, and reacted with an array of amplification sites under exclusion amplification conditions such that the filler nucleotide sequence(s) fills the amplification sites. Exemplary configurations that can be used to allow the filler sequences to be amplified while prohibiting amplification of the target sequence include, for example, a single target molecule having a first region with filler sequences flanked by binding sites for amplification primers present at the amplification site and a second region having a target sequence outside of the flanked region. In another configuration, a target nucleic acid can include separate molecules or strands that carry the target sequence and filler sequence(s), respectively. The separate molecules or strands can be attached to a particle or formed as arms of a nucleic acid dendrimer or other branched structure.

In a particular embodiment, an array having amplification sites that each contain both filler sequences and a target sequence can be detected using a primer extension assay or sequencing-by-synthesis technique. In such cases, specific extension can be achieved at the target nucleotide sequence as opposed to at the large amount of filler sequence by use of appropriately placed primer binding sites. For example, binding sites for sequencing primers can be placed upstream of the target sequence and can be absent from any of the filler sequences. Alternatively, or additionally, the target sequence can include one or more non-native nucleotide analogs that are not capable of hydrogen bonding to standard nucleotides. The non-native nucleotide(s) can be placed downstream of the primer binding site (e.g. in the target sequence or in a region intervening the target sequence and the primer biding site) and as such will prevent extension or sequencing-by-synthesis until an appropriate nucleotide partner (i.e. one capable of hydrogen bonding to the non-native analog(s) in the target sequence) is added. The nucleotide analogs isocytosine (isoC) and isoguanine (isoG) are particularly useful since they pair specifically with each other but not with other standard nucleotides used in most extension and sequencing-by-synthesis techniques. A further benefit of using isoC and/or isoG in a target sequence or upstream of the target sequence is to prevent unwanted amplification of the target sequence during amplification steps by omitting the respective partner from the nucleotide mixture used for amplification.

It will be understood that an array of the present disclosure, for example, having been produced by a method set forth herein, need not be used for a detection method. Rather, the array can be used to store a nucleic acid library. Accordingly, the array can be stored in a state that preserves the nucleic acids therein. For example, an array can be stored in a desiccated state, frozen state (e.g. in liquid nitrogen), or in a solution that is protective of nucleic acids. Alternatively, or additionally, the array can be used to replicate a nucleic acid library. For example, an array can be used to create replicate amplicons from one or more of the sites on the array.

Several embodiments of the disclosure have been exemplified herein with regard to transporting target nucleic acids to amplification sites of an array and making copies of the captured target nucleic acids at the amplification sites. Similar methods can be used for non-nucleic acid target molecules. Thus, methods set forth herein can be used with other target molecules in place of the exemplified target nucleic acids. For example, a method of the present disclosure can be carried out to transport individual target molecules from a population of different target molecules. Each target molecule can be transported to (and in some cases captured at) an individual site of an array to initiate a reaction at the site of capture. The reaction at each site can, for example, produce copies of the captured molecule or the reaction can alter the site to isolate or sequester the captured molecule. In either case, the end result can be sites of the array that are each pure with respect to the type of target molecule that is present from a population that contained different types of target molecules.

In particular embodiments that use target molecules other than nucleic acids, a library of different target molecules can be made using a method that exploits exclusion amplification. For example, a target molecule array can be made under conditions where sites of the array are randomly seeded with target molecules from a solution and copies of the target molecule are generated to fill each of the seeded sites to capacity. In accordance with the exclusion amplification methods of the present disclosure, the seeding and copying processes can proceed simultaneously under conditions where the rate at which copies are made exceeds the seeding rate. As such, the relatively rapid rate at which copies are made at a site that has been seeded by a first target molecule will effectively exclude a second target molecule from seeding the site. In some cases, seeding of a target molecule will initiate a reaction that fills a site to capacity by a process other than copying of the target molecule. For example, the capture of a target molecule at a site can initiate a chain reaction that eventually renders the site incapable of capturing a second target molecule. The chain reaction can occur at a rate that exceeds the rate at which the target molecules are captured, thereby occurring under conditions of exclusion amplification.

As exemplified for target nucleic acids, exclusion amplification when applied to other target molecules can exploit a relatively slow rate for initiating a repetitive reaction (e.g. a chain reaction) at a site of an array vs. a relatively rapid rate for continuing the repetitive reaction once initiated. In the example of the previous paragraph, exclusion amplification occurs due to the relatively slow rate of target molecule seeding (e.g. relatively slow diffusion) vs. the relatively rapid rate at which a reaction occurs, for example, to fill the site with copies of the target molecule seed. In another exemplary embodiment, exclusion amplification can occur due to a delay in the formation of a first copy of a target molecule that has seeded a site (e.g. delayed or slow activation) vs. the relatively rapid rate at which subsequent copies are made to fill the site. In this example, an individual site may have been seeded with several different target molecules. However, first copy formation for any given target molecule can be activated randomly such that the average rate of first copy formation is relatively slow compared to the rate at which subsequent copies are generated. In this case, although an individual site may have been seeded with several different target molecules, exclusion amplification will allow only one of those target molecules to be copied.

Accordingly, the present disclosure provides a method for making an array of molecules that can include the steps of (a) providing a reagent including (i) an array of sites, and (ii) a solution having a plurality of different target molecules, wherein the number of the target molecules in the solution exceeds the number of sites in the array, wherein the different target molecules have fluidic access to the plurality of sites, and wherein each of the sites comprises a capacity for several target molecules in the plurality of different target molecules; and (b) reacting the reagent to produce a plurality of sites that each have a single target molecule from the plurality or to produce a plurality of sites that each have a pure population of copies from an individual target molecule from the solution, wherein the reacting includes simultaneously (i) transporting the different molecules to the sites at an average transport rate, and (ii) initiating a reaction that fills the site to capacity at an average reaction rate, wherein the average reaction rate exceeds the average transport rate. In some embodiments, step (b) can instead be carried out by reacting the reagent to produce a plurality of sites that each have a single target molecule from the plurality or to produce a plurality of sites that each have a pure population of copies from an individual target molecule from the solution, wherein the reacting includes (i) initiating a repetitive reaction (e.g. a chain reaction) to form a product from the target molecule at each of the sites, and (ii) continuing the reaction at each of the sites to form subsequent products, wherein the average rate at which the reaction occurs at the sites exceeds the average rate at which the reaction is initiated at the sites.

In the non-nucleic acid embodiments above, the target molecule can be an initiator of a repetitive reaction that occurs at each site of the array. For example, the repetitive reaction can form a polymer that precludes other target molecules from occupying the site. Alternatively, the repetitive reaction can form one or more polymers that constitute molecular copies of a target molecule that was transported to the site.

EXEMPLARY EMBODIMENTS

Embodiment 1

A method for amplifying nucleic acids, comprising
(a) providing an amplification reagent comprising
   (i) an array of amplification sites,
   wherein the amplification sites comprise two populations of capture nucleic acids, each population comprising a capture sequence,
   wherein a first population comprises a first capture sequence and a second population comprises a second capture sequence, and
   (ii) a solution comprising a plurality of different modified double-stranded target nucleic acids,
   wherein the different modified target nucleic acids comprise at the 3' end a first universal capture binding sequence having less affinity for the first capture sequence than a first universal capture binding sequence having 100% complementarity with the first capture sequence; and
(b) reacting the amplification reagent to produce a plurality of amplification sites that each comprise a clonal population of amplicons from an individual target nucleic acid from the solution.

Embodiment 2

A method for amplifying nucleic acids, comprising
(a) providing an amplification reagent comprising
   (i) an array of amplification sites,
   wherein the amplification sites comprise two populations of capture nucleic acids, each population comprising a capture sequence,
   wherein a first population comprises a first capture sequence and a second population comprises a second capture sequence, and
   (ii) a solution comprising a plurality of different modified target nucleic acids,
   wherein the different modified target nucleic acids comprise at the 3' end a first universal capture binding sequence having less affinity for the first capture sequence than a first universal capture binding sequence having 100% complementarity with the first capture sequence; and
(b) reacting the amplification reagent to produce a plurality of amplification sites that each comprise a clonal population of amplicons from an individual target nucleic acid from the solution, wherein the reacting comprises
   (i) producing a first amplicon from an individual target nucleic acid that transports to each of the amplification sites, and
   (ii) producing subsequent amplicons from the individual target nucleic acid that transports to each of the amplification sites or from the first amplicon,
wherein the average rate at which the subsequent amplicons are generated at the amplification sites is less than the average rate at which the first amplicon is generated at the amplification sites.

Embodiment 3

A method for determining nucleic acid sequences, comprising performing a sequencing procedure that detects an apparently clonal population of amplicons at each of a plurality of amplicon sites on an array, wherein the array is made by a process that comprises:
(a) providing an amplification reagent comprising
   (i) a plurality of amplification sites,
   wherein the amplification sites comprise two populations of capture nucleic acids, each population comprising a capture sequence,
   wherein a first population comprises a first capture sequence and a second population comprises a second capture sequence, and
   (ii) a solution comprising a plurality of different modified target nucleic acids,
   wherein the different modified target nucleic acids comprise at the 3' end a first universal capture binding sequence having less affinity for the first capture sequence than a first universal capture binding sequence having 100% complementarity with the first capture sequence; and
(b) reacting the amplification reagent.

Embodiment 4

The method of any one of Embodiments 1-3, wherein the number of the different modified target nucleic acids in the solution exceeds the number of amplification sites in the array,
   wherein the different modified target nucleic acids have fluidic access to the plurality of amplification sites, and
   wherein each of the amplification sites comprises a capacity for several nucleic acids in the plurality of different nucleic acids

Embodiment 5

The method of any one of Embodiments 1-4, wherein the reacting comprises simultaneously
   (i) transporting the different modified target nucleic acids to the amplification sites at an average transport rate, and
   (ii) amplifying the target nucleic acids that are at the amplification sites at an average amplification rate, wherein the average amplification rate is less than the average transport rate.

Embodiment 6

The method of any one of Embodiments 1-5, wherein the plurality of different modified target nucleic acids in the solution is at a concentration that results in simultaneously:

(i) transporting the different modified target nucleic acids from the solution to the amplification sites, and (ii) amplifying the target nucleic acids that are at the amplification sites at an amplification rate to produce an array of amplicon sites that each comprise the apparently clonal population of amplicons.

Embodiment 7

The method of any one of Embodiments 1-6, wherein the first universal capture binding sequence has less than 100% complementarity with the first capture sequence.

Embodiment 8

The method of any one of Embodiments 1-7, wherein the first universal capture binding sequence comprises 1, 2, or 3 nucleotides that are non-complementary to the first capture sequence.

Embodiment 9

The method of any one of Embodiments 1-8, wherein the different modified target nucleic acids comprise a heterogeneous population of first universal capture binding sequences, wherein the heterogeneous population comprises individual first universal capture binding sequences having (i) 1, 2, or 3 nucleotides that are non-complementary to the first capture sequence, or (ii) 100% complementarity with the first capture sequence.

Embodiment 10

The method of any one of Embodiments 1-9, wherein the members of the heterogeneous population having 100% complementarity with the first capture sequence are present at a greater number than the other members of the heterogeneous population.

Embodiment 11

The method of any one of Embodiments 1-10, wherein the first universal capture binding sequence has a length that is less than the length of the first capture sequence.

Embodiment 12

The method of any one of Embodiments 1-11, wherein the first universal capture binding sequence have a length that is from 1 to 12 nucleotides less than the length of the first capture sequence.

Embodiment 13

The method of any one of Embodiments 1-12, wherein the different modified target nucleic acids comprise a heterogeneous population of first universal capture binding sequences, wherein the heterogeneous population comprises individual first universal capture binding sequences having from 1 to 12 nucleotides less than the length of the first capture sequence.

Embodiment 14

The method of any one of Embodiments 1-13, wherein the heterogeneous population further comprises individual first universal capture binding sequences having (iii) a length that is less than the length of the first capture sequence.

Embodiment 15

The method of any one of Embodiments 1-14, wherein individual first universal capture binding sequences have a length that is from 1 to 12 nucleotides less than the length of the first capture sequence.

Embodiment 16

The method of any one of Embodiments 1-15, wherein individual members of the heterogeneous population having a length that is less than the length of the first capture sequence comprise 1, 2, or 3 nucleotides that are non-complementary to the sequence of the first capture sequence, or 100% complementarity with the sequence of the first capture sequence.

Embodiment 17

The method of any one of Embodiments 1-16, wherein the different modified target nucleic acids comprise at the 5' end a second universal capture binding sequence having a complement that has less affinity for the second capture sequence than a second universal capture binding sequence having a complement with 100% complementarity to the second capture sequence.

Embodiment 18

The method of any one of Embodiments 1-17, wherein the complement of the second universal capture binding sequence has less than 100% complementarity with the second capture sequence.

Embodiment 19

The method of any one of Embodiments 1-18, wherein the complement of the second universal capture binding sequence comprises 1, 2, or 3 nucleotides that are non-complementary to the second capture sequence.

Embodiment 20

The method of any one of Embodiments 1-19, wherein the different modified target nucleic acids comprise a heterogeneous population of second universal capture binding sequences, wherein the heterogeneous population comprises individual second universal capture binding sequences comprising a complement having (i) 1, 2, or 3 nucleotides that are non-complementary to the second capture sequence, or (ii) 100% complementarity with the second capture sequence.

Embodiment 21

The method of any one of Embodiments 1-20, wherein the members of the heterogeneous population comprising a complement having 100% complementarity with the second capture sequence are present at a greater number than the other members of the heterogeneous population.

Embodiment 22

The method of any one of Embodiments 1-21, wherein the second universal capture binding sequence has a length that is less than the length of the second capture sequence.

Embodiment 23

The method of any one of Embodiments 1-22, wherein the second universal capture binding sequence has a length that is from 1 to 12 nucleotides less than the length of the second capture sequence.

Embodiment 24

The method of any one of Embodiments 1-23, wherein the different modified target nucleic acids comprise a heterogeneous population of second universal capture binding sequences, wherein the heterogeneous population comprises individual second universal capture binding sequences having from 1 to 12 nucleotides less than the length of the second capture sequence.

Embodiment 25

The method of any one of Embodiments 1-24, wherein the heterogeneous population further comprises individual second universal capture binding sequences having (iii) a length that is less than the length of the second capture sequence.

Embodiment 26

The method of any one of Embodiments 1-25, wherein individual second universal capture binding sequences have a length that is from 1 to 12 nucleotides less than the length of the second capture sequence.

Embodiment 27

The method of any one of Embodiments 1-26, wherein the individual members of the heterogeneous population having a length that is less than the length of the second capture sequence comprise a complement comprising 1, 2, or 3 nucleotides that are non-complementary to the sequence of the second capture sequence, or 100% complementarity with the sequence of the second capture sequence.

Embodiment 28

The method of any one of Embodiments 1-27, wherein the target nucleic acid is DNA.

Embodiment 29

The method of any one of Embodiments 1-28, wherein the array of amplification sites comprises an array of features on a surface.

Embodiment 30

The method of any one of Embodiments 1-29, wherein the area for each of the features is greater than the diameter of the excluded volume of the target nucleic acids that are transported to the amplification sites.

Embodiment 31

The method of any one of Embodiments 1-30, wherein the features are non-contiguous and are separated by interstitial regions of the surface that lack the capture agents.

Embodiment 32

The method of any one of Embodiments 1-31, wherein each of the features comprises a bead, well, channel, ridge, projection or combination thereof.

Embodiment 33

The method of any one of Embodiments 1-2, wherein the array of amplification sites comprises beads in solution or beads on a surface.

Embodiment 34

The method of any one of Embodiments 1-3, wherein the amplifying of the target nucleic acids that are transported to the amplification sites occurs isothermally.

Embodiment 35

The method of any one of Embodiments 1-34, wherein the amplifying of the different modified target nucleic acids that are transported to the amplification sites does not include a denaturation cycle.

Embodiment 36

The method of any one of Embodiments 1-35, wherein the plurality of amplification sites that comprise a clonal population of amplicons exceeds 40% of the amplification sites for which the different modified target nucleic acids had fluidic access during (b).

Embodiment 37

The method of any one of Embodiments 1-36, wherein a sufficient number of amplicons are generated from the individual target nucleic acids at the individual amplification sites respectively to fill the capacity of the respective amplification site during (b).

Embodiment 38

The method of any one of Embodiments 1-37, wherein the rate at which the amplicons are generated to fill the capacity of the respective amplification site is less than the rate at which the individual target nucleic acids are transported to the individual amplification sites respectively.

Embodiment 39

The method of any one of Embodiments 1-38, wherein the transporting comprises passive diffusion.

Embodiment 40

The method of any one of Embodiments 1-39, wherein the amplification reagent further comprises a polymerase and a recombinase.

Embodiment 41

A method for producing a library, comprising:

providing a solution of a plurality of double-stranded target nucleic acids;

ligating a universal adapter to both ends of the double-stranded target nucleic acids to form a first plurality of modified target nucleic acids, wherein each of the modified target nucleic acids comprises a target nucleic acid flanked by the universal adapter, wherein the universal adapter comprises (i) a region of double stranded nucleic acid, and (ii) a region of single-stranded non-complementary nucleic acid strands comprising a universal capture binding sequence at the 3' end, wherein the universal capture binding sequence comprises a heterogeneous population, and wherein the ligating covalently attaches the region of double stranded nucleic acid of the universal adapter to each end of the double-stranded target fragments.

Embodiment 42

The method of Embodiment 41, wherein the members of the heterogeneous population of universal capture binding sequences at the 3' end differ from each other at 1, 2, or 3 nucleotides.

Embodiment 43

The method of Embodiment 41 or 42, wherein the members of the heterogeneous population of universal capture binding sequences at the 3' end have lengths that differ from each other by 1-12 nucleotides.

Embodiment 44

The method of any one of Embodiments 41-43, wherein the members of the heterogeneous population of universal capture binding sequences at the 3' end differ from each other at 1, 2, or 3 nucleotides, differ from each other by 1-12 nucleotides, or a combination thereof.

Embodiment 45

The method of any one of Embodiments 41-44, wherein the region of single-stranded non-complementary nucleic acid strands comprises a second universal capture binding sequence at the 5' end.

Embodiment 46

The method of any one of Embodiments 41-45, wherein the members of the heterogeneous population of second universal capture binding sequences at the 5' end differ from each other at 1, 2, or 3 nucleotides.

Embodiment 47

The method of any one of Embodiments 41-46, wherein the members of the heterogeneous population of second universal capture binding sequences at the 5' end have lengths that differ from each other by 1-12 nucleotides.

Embodiment 48

The method of any one of Embodiments 41-47, wherein the members of the heterogeneous population of second universal capture binding sequences at the 5' end differ from each other at 1, 2, or 3 nucleotides, differ from each other by 1-12 nucleotides, or a combination thereof.

Embodiment 49

A composition comprising an array of amplification sites and at least one target nucleic acid bound to an amplification site, wherein the amplification sites comprise two populations of capture nucleic acids, each population comprising a capture sequence, wherein a first population comprises a first capture sequence and a second population comprises a second capture sequence, wherein the target nucleic acid comprises at the 3' end a first universal capture binding sequence having less affinity for the first capture sequence than a first universal capture binding sequence having 100% complementarity with the first capture sequence, wherein the target nucleic acid universal capture binding sequence is hybridized to the first capture sequence.

Embodiment 50

The composition of Embodiment 49, wherein the first universal capture binding sequence has less than 100% complementarity with the first capture sequence.

Embodiment 51

The composition of Embodiment 49 or 50, wherein the first universal capture binding sequence comprises 1, 2, or 3 nucleotides that are non-complementary to the first capture sequence.

Embodiment 52

The composition of any one of Embodiments 49-51, wherein at least 30% of the amplification sites of the array are occupied by at least one target nucleic acid.

Embodiment 53

The composition of any one of Embodiments 49-52, wherein the first universal capture binding sequence comprises a heterogeneous population, wherein the heterogeneous population comprises individual first universal capture binding sequences having (i) 1, 2, or 3 nucleotides that are non-complementary to the first capture sequence, or (ii) 100% complementarity with the first capture sequence, and wherein members of the heterogeneous population are bound to different amplification sites.

Embodiment 54

The composition of any one of Embodiments 49-53, wherein the members of the heterogeneous population having 100% complementarity with the first capture sequence are present at a greater number than the other members of the heterogeneous population.

Embodiment 55

The method of any one of Embodiments 49-54, wherein the second universal capture binding sequence has a length that is less than the length of the second capture sequence.

Embodiment 56

The composition of any one of Embodiments 49-55, wherein the second universal capture binding sequence has a length that is from 1 to 12 nucleotides less than the length of the second capture sequence.

Embodiment 57

The composition of any one of Embodiments 49-56, wherein the composition comprises a plurality of different target nucleic acids, the different target nucleic acids comprising a heterogeneous population of first universal capture binding sequences, wherein the heterogeneous population comprises individual first universal capture binding sequences having from 1 to 12 nucleotides less than the length of the first capture sequence.

Embodiment 58

The composition of any one of Embodiments 49-57, wherein the heterogeneous population further comprises individual first universal capture binding sequences having (iii) a length that is less than the length of the first capture sequence.

Embodiment 59

The composition of any one of Embodiments 49-58, wherein individual first universal capture binding sequences comprising a reduced length have a length that is from 1 to 12 nucleotides less than the length of the first capture sequence.

Embodiment 60

The composition of any one of Embodiments 49-59, wherein the individual members of the heterogeneous population having a reduced length comprise 1, 2, or 3 nucleotides that are non-complementary to the sequence of the first capture sequence, or 100% complementarity with the sequence of the first capture sequence.

Embodiment 61

The composition of any one of Embodiments 49-60, wherein the composition comprises a plurality of different target nucleic acids, the different target nucleic acids comprising at the 5' end a second universal capture binding sequence having a complement that has less affinity for the second capture sequence than a second universal capture binding sequence having a complement with 100% complementarity to the second capture sequence.

Embodiment 62

The composition of any one of Embodiments 49-61, wherein the complement of the second universal capture binding sequence has less than 100% complementarity with the second capture sequence.

Embodiment 63

The composition of any one of Embodiments 49-62, wherein the complement of the second universal capture binding sequence comprises 1, 2, or 3 nucleotides that are non-complementary to the second capture sequence.

Embodiment 64

The composition of any one of Embodiments 49-63, wherein the composition comprises a plurality of different target nucleic acids, the different target nucleic acids comprising a heterogeneous population of second universal capture binding sequences, wherein the heterogeneous population comprises individual second universal capture binding sequences comprising a complement having (i) 1, 2, or 3 nucleotides that are non-complementary to the second capture sequence, or (ii) 100% complementarity with the second capture sequence.

Embodiment 65

The composition of any one of Embodiments 49-64, wherein the members of the heterogeneous population comprising a complement having 100% complementarity with the second capture sequence are present at a greater number than the other members of the heterogeneous population.

Embodiment 66

The composition of any one of Embodiments 49-65, wherein the target nucleic acid comprises at the 5' end a second universal capture binding sequence having has a length that is less than the length of the second capture sequence.

Embodiment 67

The composition of any one of Embodiments 49-66, wherein the second universal capture binding sequence has a length that is from 1 to 12 nucleotides less than the length of the second capture sequence.

Embodiment 68

The composition of any one of Embodiments 49-67, wherein the composition comprises a plurality of different target nucleic acids, the different target nucleic acids comprising a heterogeneous population of second universal capture binding sequences, wherein the heterogeneous population comprises individual second universal capture binding sequences having from 1 to 12 nucleotides less than the length of the second capture sequence.

Embodiment 69

The composition of any one of Embodiments 49-68, wherein the heterogeneous population further comprises individual second universal capture binding sequences having (iii) a length that is less than the length of the second capture sequence.

Embodiment 70

The composition of any one of Embodiments 49-69, wherein individual second universal capture binding sequences have a length that is from 1 to 12 nucleotides less than the length of the second capture sequence.

Embodiment 71

The composition of any one of Embodiments 49-70, wherein the individual members of the heterogeneous population having a length that is less than the length of the second capture sequence comprise a complement comprising 1, 2, or 3 nucleotides that are non-complementary to the sequence of the second capture sequence, or 100% complementarity with the sequence of the second capture sequence.

Embodiment 72

The composition of any one of Embodiments 49-71, wherein the target nucleic acid is DNA.

EXAMPLES

The present invention is illustrated by the following examples. It is to be understood that the particular examples, materials, amounts, and procedures are to be interpreted broadly in accordance with the scope and spirit of the invention as set forth herein.

Example 1

General Assay Methods and Conditions

Unless otherwise noted, this describes the general assay conditions used in the Examples described herein.

Nucleic acid libraries were generated starting with standard Nextera™ library preparation to introduce the universal portion of the adapter through tagmentation of human gDNA. This universal tagmentation was then split into individual reactions, one for each of the different adapter pairs (PCR1-PCR21). In each of these reactions, Nextera™ XT library preparation reagents (Illumina, Inc., San Diego, California) were used to introduce the modified adapters through 12 cycles of PCR, by replacing the standard P5/P7 adapters with the modified ones. Modified adapters were designed with changes from the standard P5/P7 sequences (as outlined below) and synthesized by Integrated DNA Technologies (IDT Inc., Skokie, Illinois).

Example 2

Evaluation of Adapter Mutants for Kinetic Delay

A range of modified adapters were used to generate libraries which differ from the standard Nextera™ library (Table 1). These adapters were either slightly shorter than standard (−4 bp or −9 bp) or had 1, 2, or 3 mismatches ('wobble' bases: 1 W, 2 W, or 3 W respectively) introduced along the length of the P5/P7 regions. The range of mutations was from perfect P5&P7 sequences (PCR1) to 3 mismatches in both ends (PCR 21).

The concentration of each library was then quantified, and the libraries were normalized to identical concentrations. Libraries with the different modified adapters were then amplified separately on a qPCR instrument (BioRad CFX384 Real-Time System) using a KAPA Library Quantification kit for Illumina Platforms (Kapa Biosystems) with custom primers to simulate flowcell conditions to generate the results in Table 1. Efficiency was calculated from the number of cycles needed to reach Ct (threshold cycle) as standardly defined for qPCR.

TABLE 1

| Adapter number | Identity of adapter | FCP5 FCP7 Efficiency qPCR 3 |
|---|---|---|
| 1 | PCR 1 - Nex Control | 1.5079 |
| 2 | PCR 2 αβ-4 | 1.4875 |

TABLE 1-continued

| Adapter number | Identity of adapter | FCP5 FCP7 Efficiency qPCR 3 |
|---|---|---|
| 3 | PCR 3 αβ-9 | 1.5229 |
| 4 | PCR 4 - Nex P5 + 1W | 1.4305 |
| 5 | PCR 5 - Nex P5 + 2W | 1.4160 |
| 6 | PCR 6 - Nex P5 + 3W | 1.3716 |
| 7 | PCR 7 αβ-4 + 1W | 1.3577 |
| 8 | PCR 8 αβ-4 + 2W | 1.3673 |
| 9 | PCR 9 αβ-4 + 3W | 1.3273 |
| 10 | PCR 10 αβ-9 + 1W | 1.4236 |
| 11 | PCR 11 αβ-9 2W | 1.4179 |
| 12 | PCR 12 αβ-9 + 3W | 1.3691 |
| 13 | PCR 13 - 1 MM + 1MM | 1.3692 |
| 14 | PCR 14 - 1MM + 2W | 1.3789 |
| 15 | PCR 15 - 1MM + 3W | 1.3488 |
| 16 | PCR 16 - 2W + 1MM | 1.3504 |
| 17 | PCR 17 - 2W + 2W | 1.2971 |
| 18 | PCR 18 - 2W + 3W | 1.2980 |
| 19 | PCR 19 - 3W + 1MM | 1.2861 |
| 20 | PCR 20 - 3W + 2W | 1.2498 |
| 21 | PCR 21 - 3W + 3W | 1.2261 |

αβ-4 refers to four base pairs removed from adapter; αβ-9 refers to nine base pairs removed from adapter; 1W, 2W, 3W refer to 1, 2, or 3 wobble mismatches, respectively, present along the length of a region that binds to a capture nucleic acid present on the surface of an array; 1 MM, true mismatch; FCP5, FCP7, full-length P5 and P7 primers, respectively.

Example 3

Evaluation of Adapter Mutants for Kinetic Delay Using Sequencing

Different mutant adapters were chosen and run either by themselves or in groups on a HiSeq™ X flowcell (Table 2). All sequencing was performed on an Illumina HiSeq™ X instrument using standard reagent kits.

TABLE 2

| Lane of the flowcell | The adapters used in the lane |
|---|---|
| Lane 1 | PCR 1 |
| Lane 2 | PCR 2 |
| Lane 3 | PCR 18 |
| Lane 4 | PCR 6 |
| Lane 5 | PCR 10 |
| Lane 6 | PCR 1-2, 4-6, 10 |
| Lane 7 | PCR 1-2, 7-8, 10, 11 |
| Lane 8 | PCR 2, 6, 8, 12 |

Results

Figure 3A:
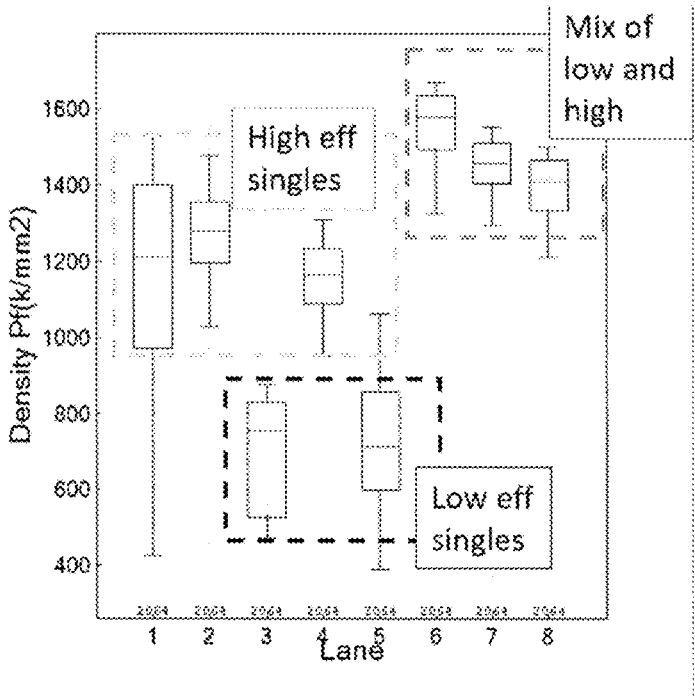
FIG. 3A shows the density passing filter of individual and groups of adapters. k/mm2, thousand per square millimeter. Lanes refer to the lanes of the flowcell shown in Table 2 of the Examples.

As shown in FIG. 3A, Lanes 1, 2, and 4 were reactions using adapters with fewer mismatches and higher efficiencies, and as expected resulted in high intensity and a high percentage of clusters which passed filter. Lanes 3 and 5 were reactions using adapters with more mismatches and lower efficiencies, and as expected resulted in low intensity and a low percentage of clusters which passed filter. Lanes 6, 7, and 8 were mixes of adapters with high and low efficiencies. Counter-intuitively, the mixtures did not perform as an average of the performance of the individual components (e.g., halfway between the high and low efficiencies) but outperformed all single-type libraries in both intensity and clusters passing filter. Thus, the surprising result is that by reducing the average homology, the rate of called monoclonality of the nanowells was improved, even though the average rate of amplification is reduced. The novelty is that a certain degree of variability is introduced into the adapter sequences, so that there is now a range of efficiencies among the population of templates. In this way, when multiple templates seed onto a pad, there is usually one which has an advantage over all the others, such that it clearly dominates the pad. Furthermore, the reduced homology is corrected in daughter copies, such that the delay introduced only to first copy, without affecting the efficiency of the later amplification.

Different mutant adapters were chosen and run either by themselves or in groups on a HiSeq™ X flowcell (Table 3). As above, all sequencing was performed on an Illumina HiSeq™ X instrument using standard reagent kits.

TABLE 3

| Lane of the flowcell | The adapters used in the lane |
| --- | --- |
| Lane 1 | PCR 1 |
| Lane 2 | PCR 3 |
| Lane 3 | PCR 10 |
| Lane 4 | PCR 16 |
| Lane 5 | PCR 1, 3, 6, 8, 9, 10, 16-18 |
| Lane 6 | PCR 21 |
| Lane 7 | PCR 1, 3, 6, 8, 9, 10, 16-18 |
| Lane 8 | PCR 1, 3, 10 |

Figure 3B:
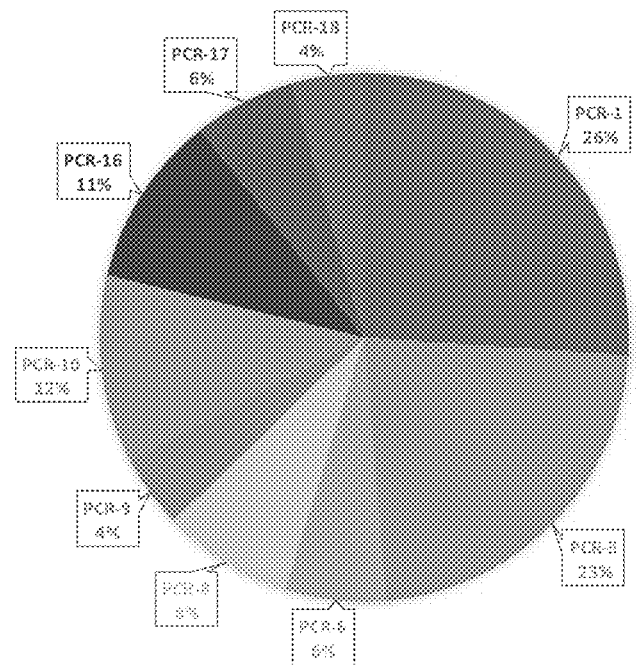
FIG. 3B shows the ratio of final reads associated with individual mutant adapters.
Figure 4A:
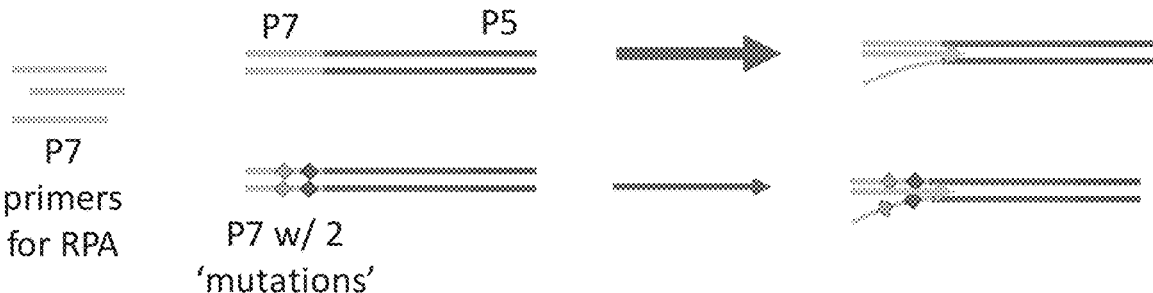
FIGS. 4A and 4B show schematics of illustrative examples of strand invasion and duplication ("RPA" refers to recombinase polymerase amplification).
Figure 4B:
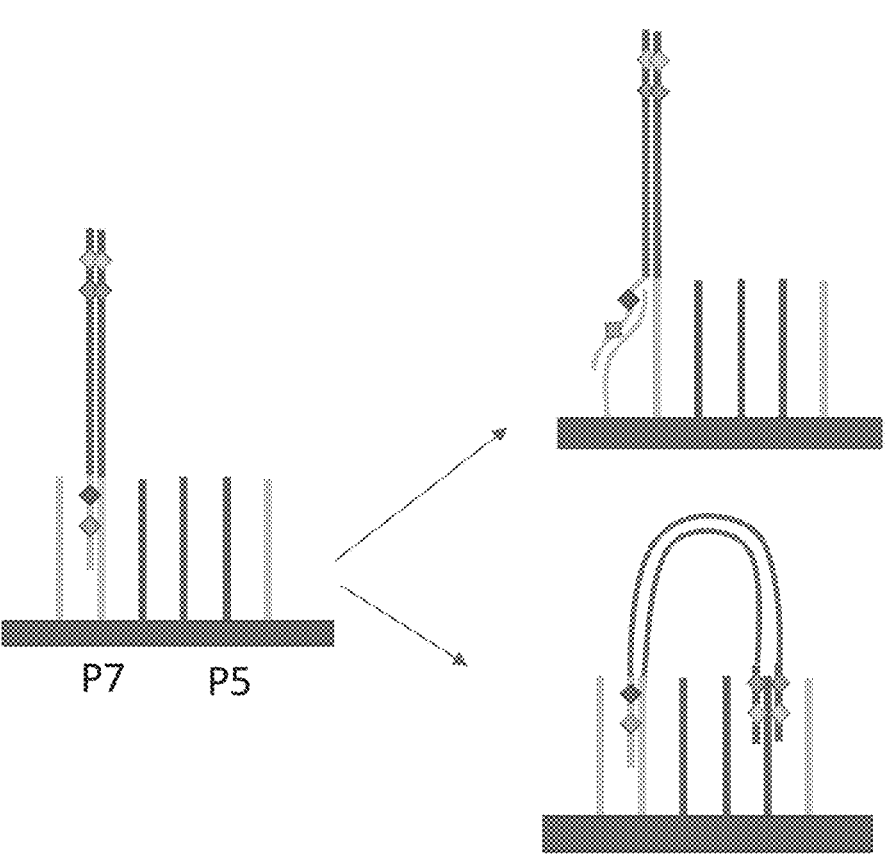
Figure 5A:
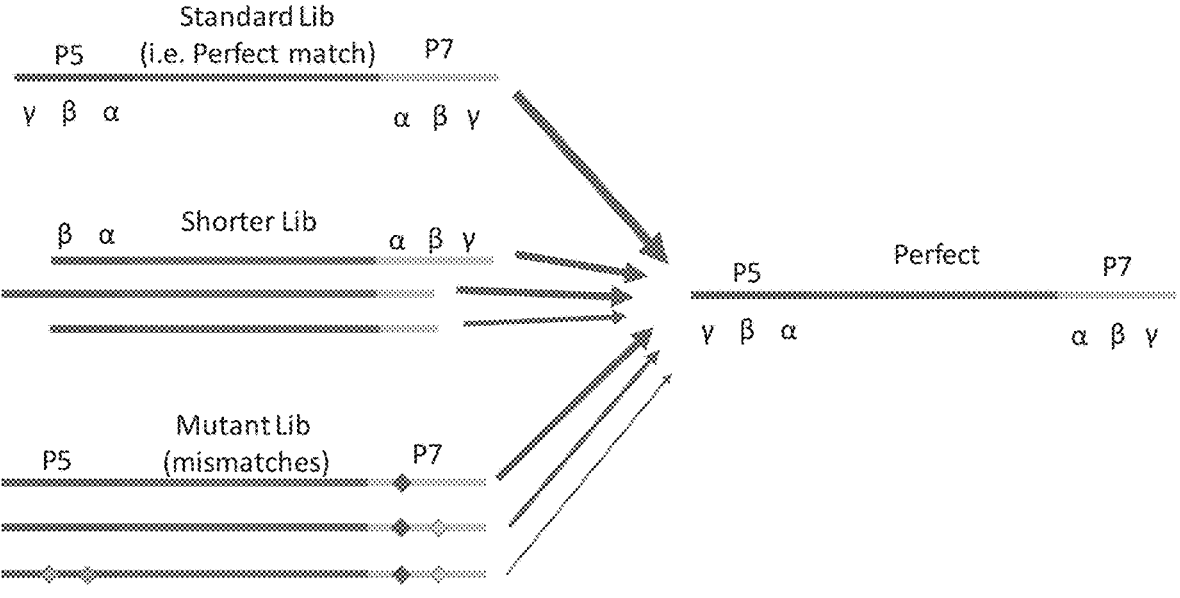
FIGS. 5A and 5B show the effects of short and mutant adapter libraries on the rates of amplification.
Figure 5B:
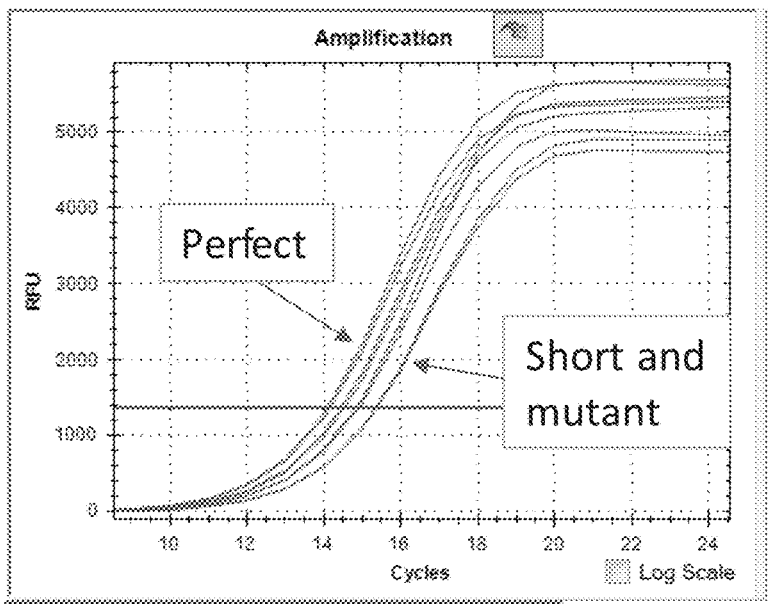
Figure 6:
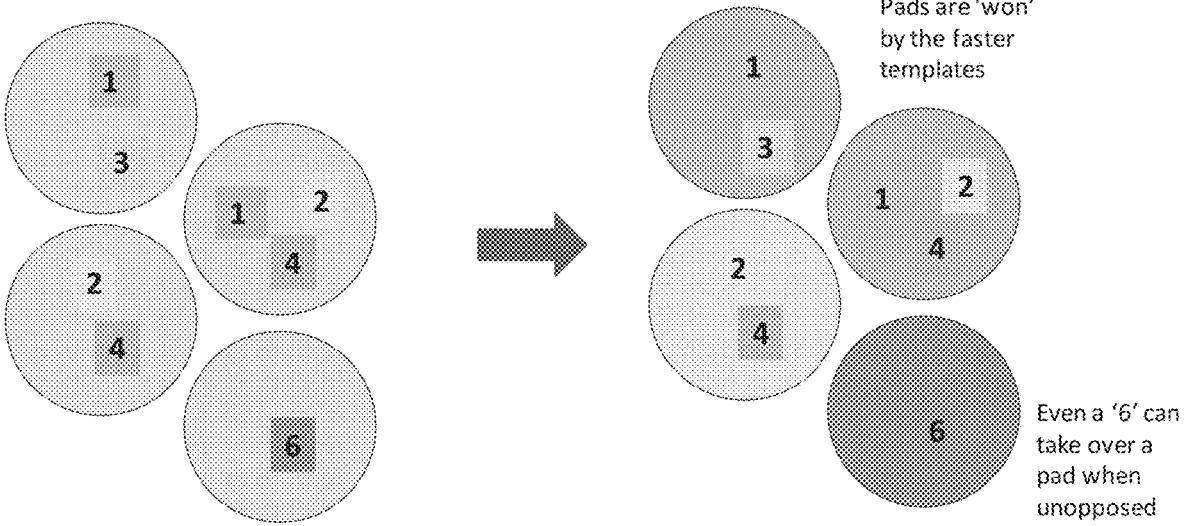
FIG. 6 illustrates competition between different templates for clonal dominance on an individual pad. Seeded templates are shown with their amplification bias (i.e. kinetic delay); 1=fastest, 6=slowest. Equal molar ratios of the templates are not necessary or even desirable. Higher numbers of the faster templates are preferred. However, even the slowest template (6) can populate a pad with a monoclonal cluster if it does not have a competition on the pad.

When a group of mutant adapters were run in a mixture (e.g. Lane 7), they were combined in equal concentrations. In a conventional sequencing run, i.e. one not using the proposed methods, equal concentrations of mixed libraries of the same adapters would result in equal ratios of reads on the flowcell. As shown in FIG. 3B, the mixture of different mutant adapters resulted in a representation of final read counts which was proportional to their efficiency and not to their seeded concentration, thus demonstrating the efficacy of the proposed method, i.e. adapters with lower affinity had longer kinetic delays, which resulted in a lower proportion of the final reads.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The disclosure is not limited to the exact details shown and described, for variations obvious to one skilled in the art will be included within the disclosure defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present disclosure. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

The invention claimed is:

1. A composition comprising an array of amplification sites and at least one target nucleic acid bound to an amplification site, wherein the amplification sites comprise two populations of capture nucleic acids attached to the amplification sites, each population comprising a capture sequence, wherein a first population comprises a first capture sequence and a second population comprises a second capture sequence, wherein the target nucleic acid comprises at the 3' end a first universal capture binding sequence having less affinity for the first capture sequence than a first universal capture binding sequence having 100% complementarity with the first capture sequence, wherein the target nucleic acid universal capture binding sequence is hybridized to the first capture sequence.

2. The composition of claim 1, wherein the first universal capture binding sequence has less than 100% complementarity with the first capture sequence.

3. The composition of claim 1, wherein the first universal capture binding sequence comprises 1, 2, or 3 nucleotides that are non-complementary to the first capture sequence.

4. The composition of claim 1, wherein at least 30% of the amplification sites of the array are occupied by at least one target nucleic acid.

5. The composition of claim 4, wherein the first universal capture binding sequence comprises a heterogeneous population, wherein the heterogeneous population comprises individual first universal capture binding sequences having (i) 1, 2, or 3 nucleotides that are non-complementary to the first capture sequence, or (ii) 100% complementarity with the first capture sequence, and wherein members of the heterogeneous population are bound to different amplification sites.

6. The composition of claim 5, wherein the members of the heterogeneous population having 100% complementarity with the first capture sequence are present at a greater number than the other members of the heterogeneous population.

7. The composition of claim 1, wherein the target nucleic acid further comprises at the 5' end a second universal capture binding sequence, wherein the second universal capture binding sequence has a length that is less than the length of the second capture sequence.

8. The composition of claim 7, wherein the second universal capture binding sequence has a length that is from 1 to 12 nucleotides less than the length of the second capture sequence.

9. The composition of claim 8, wherein the composition comprises a plurality of different target nucleic acids, the different target nucleic acids comprising a heterogeneous population of first universal capture binding sequences, wherein the heterogeneous population comprises individual first universal capture binding sequences having from 1 to 12 nucleotides less than the length of the first capture sequence.

10. The composition of claim 5, wherein the heterogeneous population further comprises individual first universal capture binding sequences having (iii) a length that is less than the length of the first capture sequence.

11. The composition of claim 10, wherein individual first universal capture binding sequences comprising a reduced length have a length that is from 1 to 12 nucleotides less than the length of the first capture sequence.

12. The composition of claim 10, wherein the individual members of the heterogeneous population having a reduced length comprise 1, 2, or 3 nucleotides that are non-complementary to the sequence of the first capture sequence, or 100% complementarity with the sequence of the first capture sequence.

13. The composition of claim 1, wherein the composition comprises a plurality of different target nucleic acids, the different target nucleic acids comprising at the 5' end a second universal capture binding sequence having a complement that has less affinity for the second capture sequence than a second universal capture binding sequence having a complement with 100% complementarity to the second capture sequence.

14. The composition of claim 13, wherein the complement of the second universal capture binding sequence has less than 100% complementarity with the second capture sequence.

15. The composition of claim 14, wherein the complement of the second universal capture binding sequence comprises 1, 2, or 3 nucleotides that are non-complementary to the second capture sequence.

16. The composition of claim 14, wherein the composition comprises a plurality of different target nucleic acids, the different target nucleic acids comprising a heterogeneous population of second universal capture binding sequences, wherein the heterogeneous population comprises individual second universal capture binding sequences comprising a complement having (i) 1, 2, or 3 nucleotides that are non-complementary to the second capture sequence, or (ii) 100% complementarity with the second capture sequence.

17. The composition of claim 14, wherein the members of the heterogeneous population comprising a complement having 100% complementarity with the second capture sequence are present at a greater number than the other members of the heterogeneous population.

18. The composition of claim 1, wherein the target nucleic acid comprises at the 5' end a second universal capture binding sequence having has a length that is less than the length of the second capture sequence.

19. The composition of claim 18, wherein the second universal capture binding sequence has a length that is from 1 to 12 nucleotides less than the length of the second capture sequence.

20. The composition of claim 18, wherein the composition comprises a plurality of different target nucleic acids, the different target nucleic acids comprising a heterogeneous population of second universal capture binding sequences, wherein the heterogeneous population comprises individual second universal capture binding sequences having from 1 to 12 nucleotides less than the length of the second capture sequence.

21. The composition of claim 16, wherein the heterogeneous population further comprises individual second universal capture binding sequences having (iii) a length that is less than the length of the second capture sequence.

22. The composition of claim 21, wherein individual second universal capture binding sequences have a length that is from 1 to 12 nucleotides less than the length of the second capture sequence.

23. The composition of claim 22, wherein the individual members of the heterogeneous population having a length that is less than the length of the second capture sequence comprise a complement comprising 1, 2, or 3 nucleotides that are non-complementary to the sequence of the second capture sequence, or 100% complementarity with the sequence of the second capture sequence.

24. The composition of claim 1, wherein the target nucleic acid is DNA.

25. The composition of claim 3, wherein each of the non-complementary nucleotides are a wobble mismatch.

26. The composition of claim 1, wherein the universal capture binding sequence has a combination of one or more mismatched nucleotides and a shortened length.

* * * * *